(12) United States Patent
Zhou et al.

(10) Patent No.: US 10,240,131 B2
(45) Date of Patent: Mar. 26, 2019

(54) TYPE II PSEUDORABIES VIRUS ATTENUATED STRAIN, ITS PREPARATION METHOD AND APPLICATION

(71) Applicant: ZHEJIANG UNIVERSITY, Hangzhou, Zhejiang Province (CN)

(72) Inventors: Jiyong Zhou, Hangzhou (CN); Gang Xing, Hangzhou (CN); Yulan Jin, Hangzhou (CN); Jinyan Gu, Hangzhou (CN); Yan Yan, Hangzhou (CN); Min Liao, Hangzhou (CN); Xiaojuan Zheng, Hangzhou (CN); Weiren Dong, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/918,547

(22) Filed: Mar. 12, 2018

(65) Prior Publication Data

US 2019/0062712 A1    Feb. 28, 2019

(30) Foreign Application Priority Data

Aug. 31, 2017   (CN) .......................... 2017 1 0774869

(51) Int. Cl.
*C12N 7/00*      (2006.01)
*A61K 39/245*    (2006.01)
*A61K 39/00*     (2006.01)

(52) U.S. Cl.
CPC .............. *C12N 7/00* (2013.01); *A61K 39/245* (2013.01); *A61K 2039/5252* (2013.01); *A61K 2039/5254* (2013.01); *A61K 2039/552* (2013.01)

(58) Field of Classification Search
None
See application file for complete search history.

(56) References Cited

U.S. PATENT DOCUMENTS

| 5,240,703 A    * | 8/1993 | Cochran ............... A61K 39/245 424/205.1 |
| 2006/0039923 A1* | 2/2006 | Chien .................. A61K 39/102 424/190.1 |

OTHER PUBLICATIONS

Wu et al. (Journal of Biotechnology. May 2016; 229-58-64).*

* cited by examiner

*Primary Examiner* — Shanon A. Foley
(74) *Attorney, Agent, or Firm* — Jiwen Chen

(57) ABSTRACT

The present invention discloses a type II Pseudorabies virus attenuated strain and its preparation method and application. The attenuated strain of pseudorabies virus is gE/TK-double-deficient strain, which is named as PRV-HD/c strain of PRV dual-deletion strain, and the accession number is CGMCC No. 14325. The attenuated strain of the pseudorabies virus of the present invention is obtained from the newly isolated strain of pseudorabies virus type II after deletion of the gE and TK double genes and has reduced pathogenicity and strong immunogenicity and is inactivated by the attenuated strain of pseudorabies virus vaccines or live attenuated vaccines, which can provide effective immunity to PRV susceptible animals such as pigs and mice.

7 Claims, 7 Drawing Sheets
Specification includes a Sequence Listing.

TYPE II PSEUDORABIES VIRUS ATTENUATED STRAIN, ITS PREPARATION METHOD AND APPLICATION

This application claims the priority benefit of Chinese Application No. 201710774869.5, filed Aug. 31, 2017 in Chinese, which is hereby incorporated by reference.

TECHNICAL FIELD

The present invention relates to the field of biotechnology, in particular to a type II Pseudorabies virus (PRV) attenuated strain and its preparation method and application.

BACKGROUND TECHNOLOGY

Pseudorabies is an acute infectious disease of pigs caused by pseudorabies virus (PRV). The outbreak of the disease in pigs can cause miscarriage in pregnancy sows, stillbirths, infertility of male pigs, mass death of newborn piglets, breathing difficulties and growth retardation of feeder pigs, etc. Pseudorabies is one of the major infectious diseases that endanger the global pig industry. It has brought tremendous economic losses to the world pig industry. At present, many European countries have announced the eradication of pseudorabies by vaccination combined with related serological diagnostic techniques. China also effectively controls the epidemic trend of PRV by vaccination. However, in 2011, pseudorabies was prevalent in China even though affected pigs were immunized with pseudorabies vaccine.

The pseudorabies virus is a herpesviridae virus with a circular envelope having a 150-180 nm diameter. The nucleocapsid is mainly composed of proteins encoded by UL19 gene and UL35 gene. There are tegument proteins between the nucleocapsid and the capsid, and at least 14 proteins are derived from the viral genome. The eleven (11) glycoproteins gb, gC, gD, gE, gG, gH, gI, gK, gL, gM and gN that have been identified for their functions. Proteins gB, gD, gH and gL are essential glycoproteins for in vitro replication and infection, and related to PRV nerve conduction. Proteins gC, gE, gG and gM are non-essential glycoprotein for virus replication, wherein gC, gE and gI are related to the PRV in the conduction direction among nerve cells. The virulence of PRV is controlled by a combination of multiple genes. The virulence-related genes are UL10, UL13, UL21, UL23 (TK), UL39/40, UL44, UL50 of UL region, US7, US8. Among them, the deletion of TK or PK leads to a significant decrease of virus virulence.

The gE gene is the encoded product of the US8 gene and is one of the six structural proteins found in the viral envelope. The gE protein is a glycoprotein that promotes cell fusion, promotes the fusion of virus-infected cells with neighboring normal cells, and participates in the spread of the virus among cells and the release of PRV virions. Numerous studies have shown that the absence of gE, although not significantly affecting the $LD_{50}$ of the virus, can reduce the neurotropic nature of the virus without affecting its immunogenicity.

TK gene is located in the UL23 region, about 900 bp in length, encoding 297 amino acids, and is a major virulence gene of herpes virus. TK is not an essential gene for PRV growth, but plays a key role in the proliferation, replication, latent infection and resurrection of PRV in the host nerve tissue cells and is mainly involved in the replication and latent infection of PRV. The absence of TK can lead to a much reduced virulence of PRV to pigs and ruminants. Studies have shown that immunization of mice with TK-deficient strains can withstand $10^2$-$10^3$ fold lethal dose of the parental challenge, and the loss of TK is also a key target of gene-deletion research.

As there is no effective treatment for pseudorabies, immunization with the vaccine becomes a fundamental measure to prevent and control pseudorabies. Now widely used is the vaccine made with the classical pseudorabies virus strains Bartha K61 and BUK. The Bartha K61 strain was repeatedly passed on from Bartha strain in allogeneic cells. BUK is obtained after passage of the attenuated strain of Bucharest strain through 800 generations passages for chicken embryos and chicken embryo fibroblasts, and has certain immunoprotective effects on pregnant sows and piglets. Gene-deleted vaccines are vaccines that use genetic engineering techniques to delete virulence-related genes or fragments of the PRV genome. The advantage of deleting seedlings lies in that the deletion locus is clear and the virulence recovery is not easy to occur, which can be used for distinguishing vaccine strains from wild-type strains. The vaccine is called serological "mark" vaccine and is the key to eradicating pseudorabies. At present, many countries have developed genetically modified strains of classical pseudorabies virus, which play an important role in the prevention, control and eradication of pseudorabies.

SUMMARY OF THE INVENTION

In the present invention, type II pseudorabies virus strain, which is different from the classical strain, is isolated and identified, and an attenuated strain of pseudorabies virus with two gE/TK deletions is obtained by gene engineering.

A strain of pseudorabies virus attenuated strain, designated as gE/TK-double virulent strain, was named PRV-HD/c, and deposited with China General Microbiological Culture Collection Center (CGMCC) located at No. 1 West Beichen Road, Chaoyang District, Beijing 100101, China with the accession number is CGMCC No. 14325, the deposition date was Jul. 6, 2017.

The present invention further provides a preparation method of the attenuated strain of pseudorabies virus type II, which comprises the following steps of:

(1) isolating and identifying wild-type pseudorabies virus strain, named PRV II-DX, accession number CGMCC No. 14326;

(2) obtaining the pseudorabies virus attenuated strain by virus rescue after knockdown of both gE and TK genes in the genome of PRV II-DX strain.

The preparation method and the gene knockout method are that the two genes of gE and TK are knocked out in turn in two steps by the Cre-LoxP recombination system.

The present invention also provides a method of using the attenuated pseudorabies virus in preparing a pseudorabies vaccine.

The pseudorabies vaccine is administered to PRV susceptible animals.

The pseudorabies virus susceptible animal is pig or mouse.

The present invention also provides a pseudorabies vaccine comprising the inactivated and attenuated pseudorabies virus.

The present invention further provides a pseudorabies virus inactivated vaccine, which comprises the pseudorabies virus attenuated strain.

The attenuated strain of the pseudorabies virus of the present invention is obtained from the newly isolated strain of type II pseudorabies virus after deletion of the gE and TK double genes and, the attenuated strain has reduced pathogenicity and strong immunogenicity. The attenuated strain can be used to prepare live or attenuated live vaccines that provide potent immunity to PRV-susceptible animals such as pigs and mice.

SPECIFIC EMBODIMENTS OF THE PRESENT INVENTION

Figure 1:
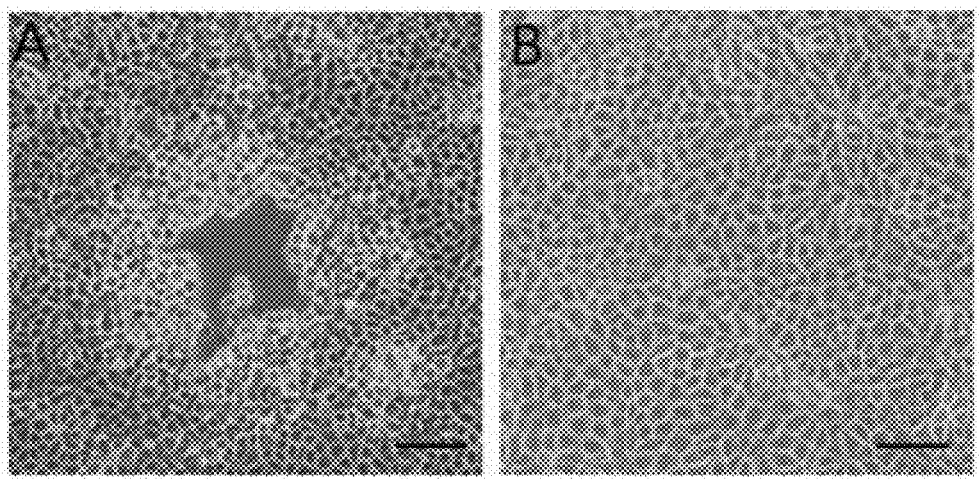
FIG. 1 is a sample of the supernatant inoculated with Vero cells in Example 1, wherein A is the experimental group, B is the negative control group.

Materials:

Clinically suspected swine pseudorabies diseased pig brain tissue disease material was: from a pig farm in Hangzhou, Zhejiang Province of China.

The PRV-SC virus is a traditional PRV strain purchased from the China Veterinary Drug Administration.

Plasmid pMCherry-C1 and plasmid pEGFP-C2 were all conserved in this laboratory. Ezup column DNA extraction kit was purchased from Shanghai Biotechnology Co., Ltd. PrimeSTAR polymerase, dNTP mix, Pyrobest high-fidelity enzyme, rTaq polymerase, 10×PCR buffer, 2×GC buffer, 100 bp Maker, PUC18 plasmid and pMD18-T Kit were purchased from Bao Bioengineering (Dalian) Co., Ltd. Fetal bovine serum was purchased from Gbico Company; MEM medium was purchased from Invitrogen; Fetal bovine serum was purchased from Hangzhou Sijiqing Biological Engineering Materials Co., Ltd.; PCR product recovery kit, gel recovery kit, plasmid kit were purchased from TIANGEN. Low melting point agar powder was purchased from Sigma Co.

Balb/c mice aged 5-6 weeks were purchased from Laboratory Animal Center of Zhejiang Province. The 8-9-week-oldand 60-day-old experimental pigs were purchased from Yuanhong Farm, Yuelong Street, Ninghai of China. The PRV, PPV, PCV2, PRRSV and CSFV antigens in the experimental pigs were negative, while the PRV and PRRSV antibodies were negative.

25 cm$^2$ and 75 cm$^2$ cell culture bottles were purchased from ORANGE SCIENTIFIC Co. of Belgium. Fluorescence Quantitation Premix ExTaq™ (Pro qPCR) was purchased from TaKaRa Co. Fluorescent PCR tubes and plates were purchased from AXYGEN. TRIzol Reagent was purchased from GIBCO; RevertAid™ First Strand cDNA Synthesis Kit was purchased from Fermentas.

Example 1

PRRSV positive material was screened by PCR and PRV was screened for the positive material grinding fluid. After sterile treatment, the supernatant was inoculated with Vero cells subculture. The refractive changes, rounding, shedding lesions of the suspected pseudorabies virus supernatant cell were observed after inoculation.

According to the gB and gE sequences of PRV in Gen-Bank, two pairs of primers gB300F, gB300R, and gE300F, gE300R were designed to amplify the conserved regions of gB and gE, respectively. Three pairs of primers gB-F/R, gC-F/R and gE-F/R were designed according to the reference sequence of PRV genome in GenBank NC_006151. Beijing Liuhe Huada Gene Technology Co., Ltd. synthesized the primer sequence shown in Table 1.

TABLE 1

| Primer Name | Primer Sequence (5'-3') | Product Length |
|---|---|---|
| gB300F | CGGCAAGTGCGTCTCCAAG (SEQ ID NO: 1) | 296 bp |
| gB300R | AGGGCGAAGGAGTCGTAGGG (SEQ ID NO: 2) | |
| gE300-F | GCTCTGCGTGCTGTGCTCC (SEQ ID NO: 3) | 332 bp |
| gE300-R | TCGTCACTTCCGGTTTCTCC (SEQ ID NO: 4) | |
| gE-F | TTTTATCTCCGTCCGCGCCGTTT (SEQ ID NO: 5) | 1993 bp |
| gE-R | CTCGCTGTAGTAGCAGTCCGAGT (SEQ ID NO: 6) | |
| gB-F | ACAGGGCGTCGGGGTCCTCGCTCTC (SEQ ID NO: 7) | 2749 bp |
| gB-R | CGAGGCGTCATGCCCGCT (SEQ ID NO: 8) | |
| gC-F | CCGTCGCCATGTGTGCCACT (SEQ ID NO: 9) | 1639 bp |
| gC-R | ACAAACAACCGGACGCGAT (SEQ ID NO: 10) | |
| TK-F | GGGTCAAGGACGCCTTCTTAA (SEQ ID NO: 11) | 1222 bp |
| TK-R | GGCACGGCAAACTTTATTGGG (SEQ ID NO: 12) | |

In a six-well plate covered with Vero cells, the medium was discarded and the plate was washed once with a fresh medium. 1 mL of the suspected supernatant was added and the mixture was incubated at 37° C. for 60 minutes. After completion of the sensory evaluation, the supernatant was discarded and 2 mL of MEM medium supplemented with 2% fetal bovine serum was added. The cells were cultured in a 37° C. incubator containing 5% $CO_2$, and the cytopathic effect was observed daily. When 80% lesions appeared in the cells, the cells were freeze-thawed three times and centrifuged to obtain the supernatant. The obtained virus was known as the first generation.

Viral plaque purification also used Vero cells. The resulting virus solution was diluted 10 times, then added to a six-well plate covered with the Vero cells and incubated at 37° C. for 60 minutes. At the same time, they were provided with a 2% concentration of low melting point agarose and underwent high pressure sterilization. After the incubation, the high pressure 2% low melting point agarose solution and 2×MEM medium of equal volume were mixed, 2% fetal bovine serum was added. The mixture was sterile stored in a 37° C. water bath. After discarding the supernatant in the cell plate, the cell plate was washed once with the fresh medium, the prepared agarose medium mixture was added, and it was coagulated at room temperature and then put into a 37° C. incubator for 3 days. Macroscopically visible plaques were picked with a pipette pick, dissolved in 1 mL of MEM, frozen and thawed for three times after receiving poison, and then inoculated in Vero cells for propagation in preparation for the next round of plaque purification. The plaque purification operation was repeated five times and then inoculated to Vomon cells covered with monolayer. After incubation, the agar was covered. When plaques grew to the proper size, they were stained with 5% crystal violet for 1 hour. After agar was carefully taken out, the plaque morphology was observed and pictures were taken.

Figure 2:
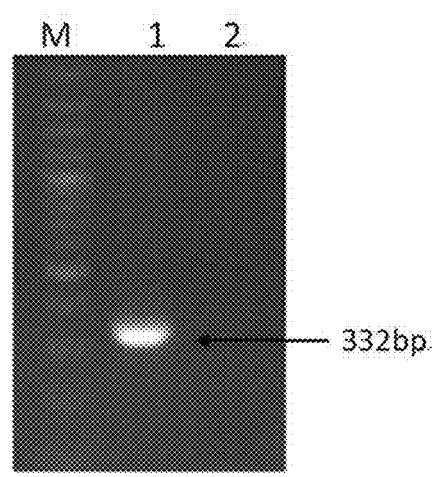
FIG. 2 is a result of amplification of gE-specific gene fragments after DNA extraction of the disease supernatant in Example 1, wherein lane M: DNA Marker, lane 1: experimental group, lane 2: negative control group.
Figure 3:
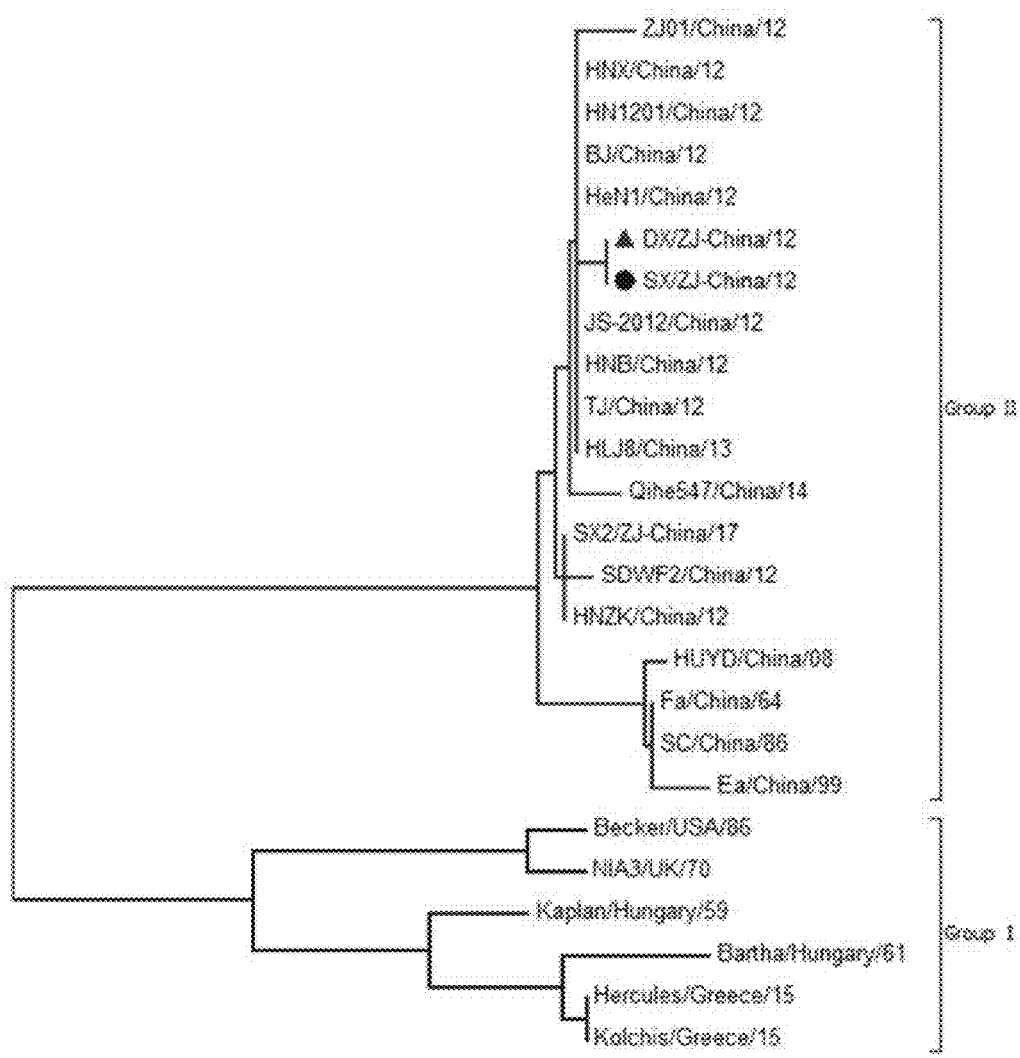
FIG. 3 is gB gene phylogenetic tree analysis results.
Figure 4:
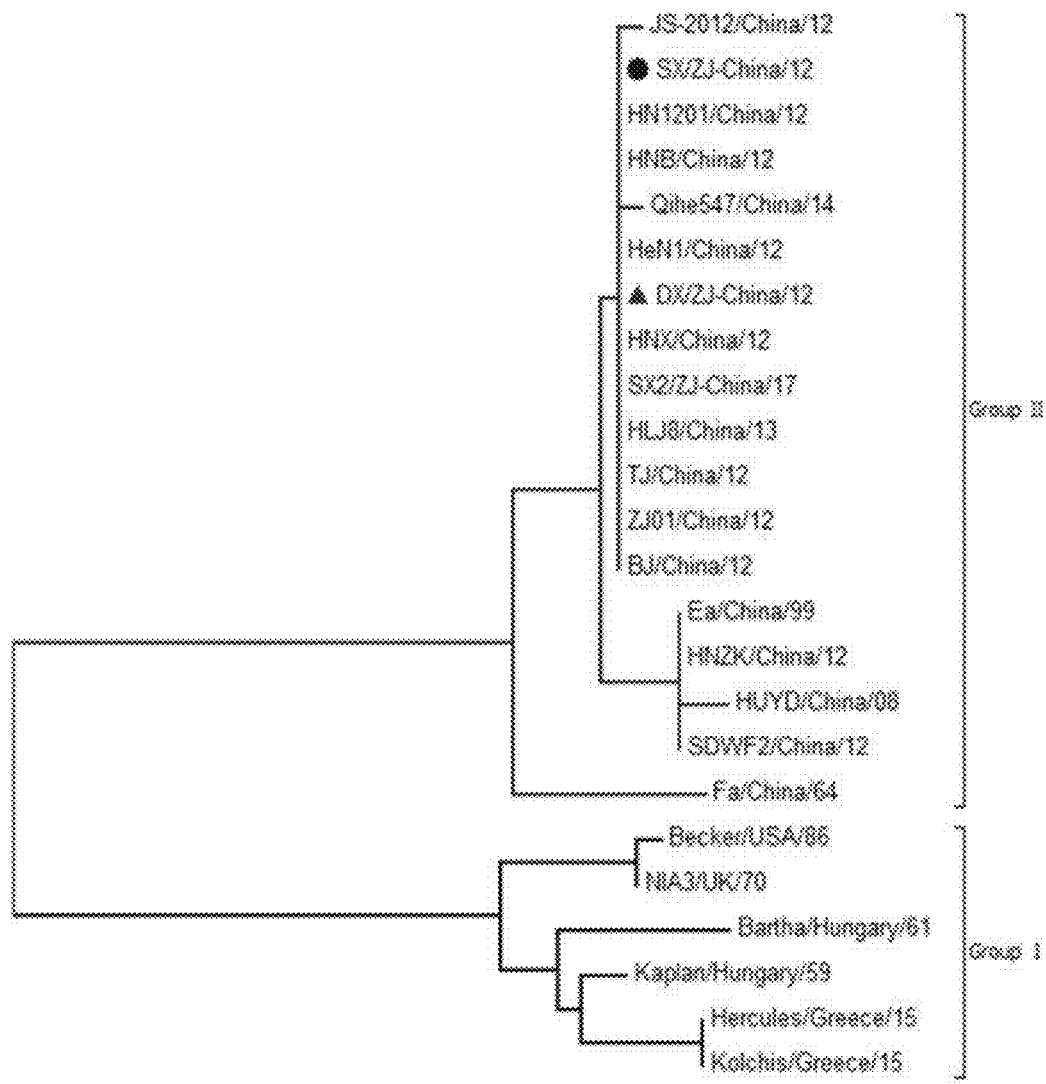
FIG. 4 is gC gene phylogenetic tree analysis results.
Figure 5:
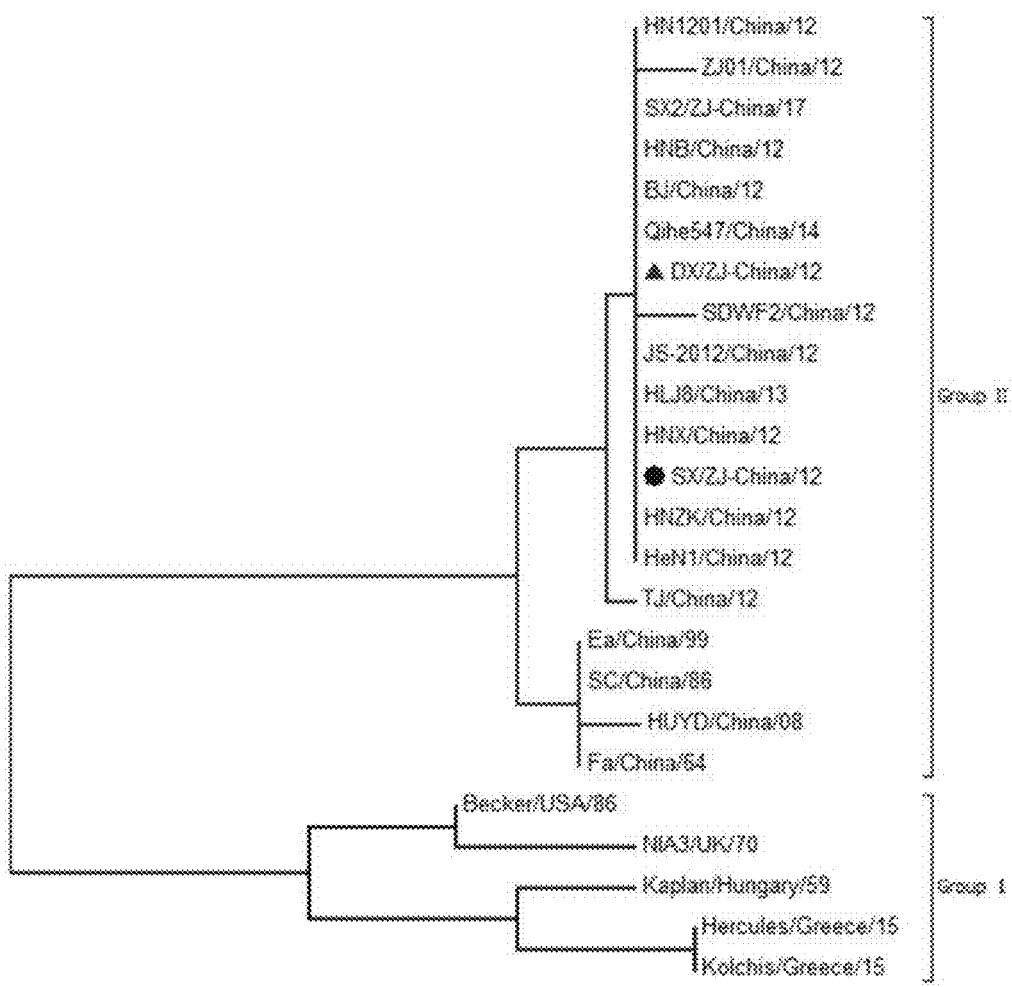
FIG. 5 is gE gene phylogenetic tree analysis results.
Figure 6:
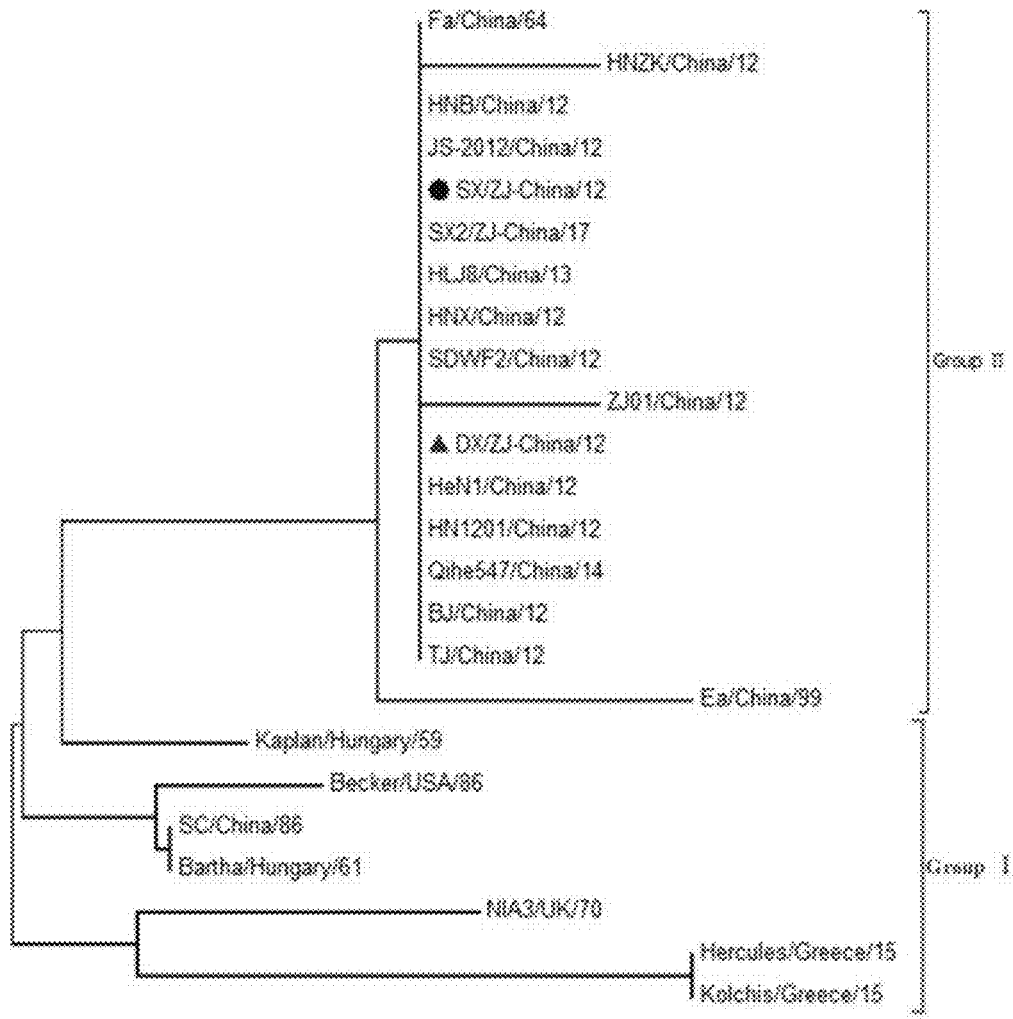
FIG. 6 is the TK gene phylogenetic tree analysis results.

After inoculating Vero cells with the supernatant of the disease material, obvious cytopathic effect was observed after 24 hours, that is, the original spindle-shaped cells began to become round and translucent and then shedding to form a plaque (see FIG. 1A) with no change in negative cells (see FIG. 1B). After the DNA was extracted from the supernatant of the diseased material and subjected to PCR detection, a gE-specific partial sequence of 332 bp was obtained after amplification (see FIG. 2), indicating that the pseudorabies virus was isolated. The isolated virus was pseudorabies virus named PRV-DX of PRV, and was sent to a depositary institution for depositary preservation and was deposited as a Chinese microorganism strain at China General Microbiological Culture Collection Center (CGMCC) located at No. 1 West Beichen Road, Chaoyang District, Beijing 100101, China with the accession number is CGMCC No. 14325, the deposition date was Jul. 6, 2017.

Example 2

Cloning and Analysis of gB, gC, gE and TK Genes of PRV-DX Strain.

The purified virus solution was used for the extraction of viral DNA as described above, and the resulting DNA solution was used as a PCR template for PCR amplification. The system (25 μL) was as follows: 2×GC buffer 12.5 dNTPmix 2 μL, primer 1 μL, template 1 μL, PrimeSTAR enzyme 0.25 μL, and finally water was added to make up to a volume of 25 μL. The PCR reaction procedure was pre-denaturation at 95° C. for 5 minutes, denaturation at 98° C. for 10 seconds, annealing at 57° C. for 20 seconds and extension at 72° C. for 2 minutes for 30 cycles. After the PCR product was detected by 1% agarose gel electrophoresis, the instruction manual of the PCR product of Sigma Co. was used to clean and recover the kit manual. The details are as follows:

In the PCR product, 3 times the volume of the product Buffer PCR-A was added (if the added buffer is less than 100 μL, make it up to 100 μL), mixed with a pipette until the mixture was mixed evenly. The mixture was then transferred to a preparation tube provided in the kit, and the preparation tube was placed in a 2 mL collection tube and centrifuged at 12000 rpm for 1 minute to discard the filtrate; the preparation tube was put back into the collection tube and 700 μL of Buffer W2 was added, 12000 rpm centrifuged for 1 minute, the filtrate was discarded; and then the preparation tube was put back to the collection tube, 400 μL of the above Buffer W2 was added, centrifuged at 12000 rpm for 1 minute, the filtrate was discarded; the preparation tube was put back to the collection tube, empty centrifuged at 12000 rpm for 1 minute. In a clean 1.5 mL centrifuge tube, 30-50 μL of TE or deionized water was added to the center of the adsorption membrane, eluted for 2 minutes at room temperature, and centrifuged for 1 minute at 12000 rpm to collect the bottom solution.

The recovered product was treated with rTaq to add poly A sticky end and incubated at 72° C. for 10 minutes. The system was as follows: 10×PCR buffer 2 μL, rTaq enzyme 0.25 μL, dNTPmix 0.5 PCR product 400 ng, and remaining water to make it to a volume of 20 μL. The above A plus tail product was ligated to pMD18T at 16° C. for 1 hour. The system was as follows: Solution I 10 μL, pMD18T 1 μL, and A-tail PCR product 9 μL.

All the above ligation products were transformed into DH5a *E. coli* competent cells and then plated onto LB solid medium plates containing ampicillin and incubated overnight at 37° C. When the colonies grew to the appropriate size, the single colonies were picked and the positive monoclonal antibodies were sent to Beijing Liuhe Huada Gene Technology Co., Ltd. for sequencing after identification of the PCR bacterial liquid.

Using MEGA5.0 software, the phylogenetic tree was obtained by comparing the gene sequence amplified by DX strain with the gene sequences of different strains downloaded from GenBank. The analysis used the neighbors method to calculate, Bootstrap value is 1000 times. At the same time, MEGA5.0 software was used to translate the previously aligned sequences into amino acid sequences and alignment analysis was conducted.

The results of phylogenetic tree (see FIG. 3, FIG. 4, FIG. 5, FIG. 6) show that the gC gene sequence of DX strain isolated in this study (SEQ ID No. 32) is consistent with the gC gene sequence of some newly isolated strains in China. They are all closer to some classical strains such as Kaplan and Becker. The same is true for the sequences of gB (SEQ ID No. 31) and gE (SEQ ID No. 33).

The results of amino acid sequence alignment showed that the gB gene of DX strain had 75-77 positions SPG three amino acid mutations inserted into the classical European strain and three SPG amino acid substitutions of 313 (V>M), 915 (S>N), mutation at position 921 (L>P). The gC gene is the insertion of seven amino acids AAASTPA consecutively at 63-69 positions. The gE gene of the DX strain differs significantly from these reference sequences by the insertion of aspartate (D) at positions 48 and 494. Position 54 is aspartic acid (D) instead of glycine (G), position 448 is isoleucine (I) instead of valine (V) and position 510 is serine (S) but not glycine (G).

Example 3

The pseudorabies virus type IIDX virus was cultured, then the whole genome of the virus was extracted, sequenced by PacBio platform, and the whole genome sequence of the virus was obtained.

QIAGEN Genomic-tip 500G was used for DNA purification of the concentrated and purified virus solution, according to the specific instructions of the kit instruction manual. OD260/OD280 and nucleic acid content and amount were detected after the extraction. Meanwhile, 0.6% agarose gel was used for electrophoresis detection. Qualified genomic DNA samples were sent to Shenzhen Huada Gene Technologies Service Co., Ltd. for sequencing and assembly. Genewise software was used to predict homologous genes based on the reference sequence JQ809328.1 to predict each ORF. Software Versions: genewise 2.2.0, Parameters: genewise, -tfor, -sum, -genesf, -gff.

Figure 7:
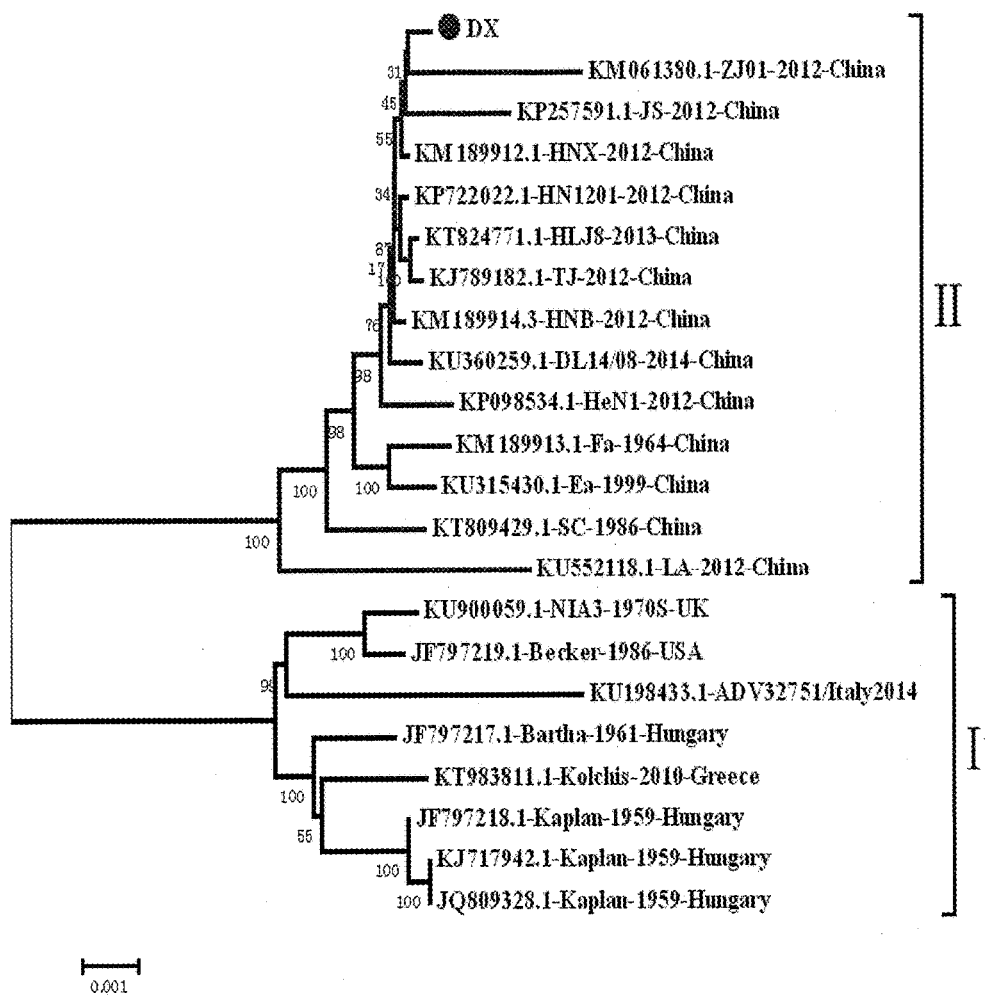
FIG. 7 shows the results of genome-wide nucleotide sequence evolution analysis.

A full length genome sequence was finally obtained. The result showed that the full genome of PRV-DX strain was 143754 bp in length and GC content was 73.59%, encoding a total of 69 open reading frames, of which US1 and IE180 were internal repeat sequences. The whole genome of PRV-DX was combined with 21 published reference strains on NCBI for genome-wide analysis. The results are shown in FIG. 7. The phylogenetic analysis showed that all PRV strains can be divided into two distinct branches. Chinese strains including PRV-DX strain belong to another branch and are named genotype II. Further analysis of Chinese strains showed that the PRV-DX strain had the closest relationship with the epidemic strains isolated in China since 2012, followed by the strains Ea, Fa and Sc and the farthest evolutionary distance from LA strain.

Genome-wide sequence analysis shows that PRV-DX strain isolated in the present invention is a type II gene and is a brand new PRV.

Example 4

A total of 70 female Balb/c mice aged 5-6 weeks were randomly divided into 7 groups, 10 mice/group. Groups 1-3 were subcutaneously injected with 0.1 mL PRV-DX (experimental group) virus solution containing $10^4$ $TCID_{50}$/mL, $10^5$ $TCID_{50}$/mL, and $10^6$ $TCID_{50}$/mL subcutaneously on the back, respectively; 4-6 groups were subcutaneously injected with 0.1 mL each of $10^4$ $TCID_{50}$/mL, $10^5$ $TCID_{50}$/mL, and $10^6$ $TCID_{50}$/mL PRV-SC strain (control group, conventional PRV strain) virus solution. Group 7 was subcutaneously inoculated with 0.1 mL of DMEM as a negative control. Within 2 weeks after challenge, the mice were continuously observed and recorded for clinical symptoms, pathology and death.

5-6 weeks old Balb/c mice were inoculated with different concentrations of PRV-DX strain and PRV-SC strain, respectively. 3-7 days after the challenge, Groups of DX $10^6$ $TCID_{50}$/mL, DX $10^5$ $TCID_{50}$/mL, SC $10^6$ $TCID_{50}$/mL group and the SC $10^5$ $TCID_{50}$/mL group all showed clinical symptoms of varying degrees of apathetic, rough hair disorder and loss of appetite. Serious bite inoculation sites were also found, leading to skin bleeding and eventually death. In the DX $10^4$ $TCID_{50}$/mL group and the SC $10^4$ $TCID_{50}$/mL group, slight clinical symptoms such as apathetic symptoms began to occur on the 4th day after challenge, and the mice died. After 7 days, the above groups of mice returned to normal, no obvious clinical symptoms appeared. Negative control mice showed normal throughout the experimental period.

According to the statistics, the death time of mice mainly concentrated on days 3-7 after challenge. The death numbers of DX $10^6$, $10^5$ and $10^4$ $TCID_{50}$/mL challenged mice were 9, 6 and 1, respectively. The death numbers of mice infected with SC $10^6$, $10^5$ and $10^4$ $TCID_{50}$/mL were 9, 4 and 1; 10 mice in the negative control group all survived normally. According to the experimental results, the $LD_{50}$ of PRV-DX strain was $10^{4.84}$ $TCID_{50}$/mL. The $LD_{50}$ of SC virulent strain in our country was $10^{5.16}$ $TCID_{50}$/mL. It indicated that the virulence of PRV-DX strain obtained from new isolation and identification was twice or more stronger than that of PRV-SC.

Example 5

Fifteen 60-day-old experimental pigs were randomly divided into three groups. The first group was inoculated with 4 mL of $10^{7.0}$ $TCID_{50}$/mL PRV-DX strain of virus solution, the second group was inoculated with 4 mL of $10^{7.0}$ $TCID_{50}$/mL PRV-SC strain of virus solution, and the negative control group was inoculated with 4 mL DMEM. Inoculation route was intranasal inoculation. These groups were subject to isolated feeding, free feeding, and continuous observation for 14 days. The temperature and clinical symptoms were recorded. The death pigs were dissected in time. Tissue sample collection, tissue sections and viral load testing were conducted.

On the second day after virus inoculation or challenge, the experimental animals with $10^{7.0}$ $TCID_{50}$/mL and $10^{7.0}$ $TCID_{50}$/mL strains of DX showed significant body temperature rise, with mean body temperature of 41.7° C. and 41.9° C., respectively. DX strain $10^{7.0}$ $TCID_{50}$/mL group showed clinical symptoms such as appetite abatement and dyspnea on the 3rd day after challenge. All the experimental animals died on the 4th day after challenge, and the lethality was 100%. On the 3rd day after challenge, SC strain $10^{7.0}$ $TCID_{50}$/mL showed only symptoms of loss of appetite. Until 14 days after challenge, only one pig died and the lethal rate was 20%. Negative control group were normal during the entire experimental period.

Experimental pigs died of experimental process or killed pigs after the end of the experiments were observed with the following general lesion findings: PRV-DX strain inoculating pig showed thickening and congestion of the brain membrane, and difficulties in separation; serious blood congestions in the brain organization; congestion and hemorrhage in lung, obvious intercostal pressure trace, slight liver congestion, and tonsil thickening congestion. There is no liver and tonsil visible macroscopic lesions in PRV-SC inoculated pigs except for slight hyperemia and swelling in brain organizations and lungs, have no. Brain, lung, liver, tonsil tissues were fixed. Paraffin sections and HE staining were conducted. The pathological sections were observed under the microscope. Capillary congestion was seen in the brain of the challenged group of PRV-DX strain, and infiltration of inflammatory cells around the blood vessels formed a typical phenomenon of "vasculitis". The focal alveolar space of the lungs became smaller and there were erythrocyte exudation, the alveolar wall had a large amount of inflammatory cell infiltration; there were visible interlobular artery congestion in the liver and tonsil inflammation infiltration seen. The PRV-SC strain challenged brain tissue also showed capillaries congestion, and a very small number of neuronal necrosis, nuclear condensation shrinkage, stained cytoplasm. There were visible alveolar wall thickening in lungs, increased inflammatory cells. No obvious lesion was observed in the liver and tonsil. The fluorescence quantitative PCR method was used to detect the gD gene fragment: upstream primer gDP-F: CACGCCGATGTG-GTGGA (SEQ ID NO: 35), downstream primer gDP-R: GGTACTGGCCCTCGTTGAA (SEQ ID NO: 36), Probe: CY5-ACTACATGTTCCCCACGGAGGACGAG-BHQ2 (SEQ ID NO: 37). The reaction system includes Premix Ex Taq qPCR): 10 μL, 0.4 μL of gDP-F, 0.4 μL of gDP-R, 0.4 μL of Probe, 6.8 μL of ddH$_2$O, and 2 μL of a template. The reaction conditions were as follows: pre-denaturation at 95° C. for 2 min, denaturation at 95° C. for 5 seconds, annealing at 55° C. for 30 seconds and extension at 60° C. for 1 min for 40 cycles, setting a negative control, using pMD18T-gD standard plasmid as a positive control, and used as the template after double dilution. After amplified by the same method, a standard curve was drawn, the corresponding copy number was calculated according to the sample CT value and the standard curve, and the viral load in each organ after inoculation of the PRV-DX strain and SC strain were calculated. The virulence of tonsil and brain was higher than that of lung and liver after challenge with PRV-DX and SC strains of the same virus content. The midbrain and lung viral load of DX strain was significantly higher than that of SC strain. The lung viral load was significantly higher than the PRV-SC group.

The PRV-DX strain PRV-DX of type II pseudorabies virus obtained by the new isolation and identification of the present invention shows much greater virulence to pigs than the classical PRV strain SC strain.

Example 6

1. Primer Design and PCR Amplification

Primers F-LgE and R-LgE, F-RgE and R-RgE were designed to amplify the homologous recombination arms flanking the gE gene (SEQ ID No. 33) with EcoRI, KpnI, BamHI and HindIII cleavage sites point. A pair of mutation primers F-Mcherry and R-Mcherry for the transformation of the pMcherry-C1 plasmid were designed and used to delete the multiple cloning site (MCS) in the plasmid so as to obtain a cherry red fluorescence complete expression cassette without MCS. A pair of primers F-McherryCPS, R-McherryCPS for amplifying a complete cherry red fluorescence complete expression cassette and a loxp sequence of the same orientation were designed to amplify the entire cherry red fluorescently integrated expression cassette. Similarly, the TK gene was designed to amplify (SEQ ID No. 34). Primers F-LTK and R-LTK, F-RTK and R-RTK on both sides of the homologous recombination arm also carry EcoRI, KpnI, BamHI and HindIII restriction sites. A pair of mutation primers F-EGFP and R-EGFP for transforming pEGFP-C2 plasmid were designed and used to delete multiple cloning sites (MCS) in plasmid to obtain an EGFP green fluorescence complete expression cassette without MCS. A pair of primers, F-EGFPCPS, R-EGFPCPS, designed to amplify the complete EGFP green fluorescence complete expression cassette, were designed and the same loxp sequence was also added upstream and downstream. The specific primer sequences are shown in Table 2. The primers were synthesized by Beijing Liuhe Huada Gene Technology Co., Ltd.

TABLE 2

Primer sequences for amplifying the corresponding fragments.

| Primer Name | Primer Sequence | introduced into the restriction site | The length of the product |
| --- | --- | --- | --- |
| F-LgE | CGGAATTCGACGATAGACGGGACGCT (SEQ ID NO: 13) | EcoRI | 1021 bp |
| R-LgE | GGGGTACCGGGTGCCCAGGTTTAAAA (SEQ ID NO: 14) | KpnI | |
| F-RgE | ACGCGTCGACCAGGACGACTCGGACTGCTAC (SEQ ID NO: 15) | BamHI | 860 bp |
| R-RgE | CCCAAGCTTGTTCAGGACGGACGACCACTC (SEQ ID NO: 16) | HindIII | |
| F-Mcherry | TACAAGTCCGGACTCGGATCTAGATAACTG (SEQ ID NO: 17) | none | 4722 bp |
| R-Mcherry | CAGTTATCTAGATCCGAGTCCGGACTTGTA (SEQ ID NO: 18) | none | |
| F-McherryCPS | GGGGTACCATAACTTCGTATAATGTATGCTATACG AAGTTATTAGTTATTAATAGTAATCAA (SEQ ID NO: 19) | KpnI | 1704 bp |
| R-McherryCPS | CGGGATCCATAACTTCGTATAGCATACATTATACG AAGTTATGATGAGTTTGGACAAACCAC (SEQ ID NO: 20) | BamHI | |
| F-LTK | CGGAATTCATCCTCCGGATCTACCTC (SEQ ID NO: 21) | EcoRI | 455 bp |
| R-LTK | GGGGTACCAGCGAGGCCACCACCAGG (SEQ ID NO: 22) | KpnI | |
| F-RTK | CGGGATCCATGGACGCGCTCGTGGCC (SEQ ID NO: 23) | BamHI | 527 bp |
| R-RTK | CCCAAGCTTAGCTGGAAGACGAACCAC (SEQ ID NO: 24) | HindIII | |
| F-EGFP | GGGGTACCAATAGTAATCAATTACGGGGTCATT (SEQ ID NO: 25) | none | 4700 bp |

TABLE 2-continued

Primer sequences for amplifying the corresponding fragments.

| Primer Name | Primer Sequence | introduced into the restriction site | The length of the product |
|---|---|---|---|
| R-EGFP | CGGGATCCAGATACATTGATGAGTTT (SEQ ID NO: 26) | none | |
| F-EGFPCPS | GGGGTACCATAACTTCGTATAATGTATGCTATACG AAGTTATAATAGTAATCAATTACGGGGTCATT (SEQ ID NO: 27) | KpnI | 1705 bp |
| R-EGFPCPS | CGGGATCCATAACTTCGTATAGCATACATTATACG AAGTTATAGATACATTGATGAGTTT (SEQ ID NO: 28) | BamHI | |

2. gE Transfer Vector Construction

The homologous recombination arms LgE and RgE of gE were amplified with primers F-LgE and R-LgE, F-RgE and R-RgE and using the PRV-DX DNA of the PRV-DX as a template. The R-PCR system comprises: 2×GC buffer 12.5 µL, dNTP mix 2 µL, primer 1 µL each, template DNA 1 µL, PrimeSTAR enzyme 0.25 µL, and finally made up to 25 µL with water. The PCR reaction procedure was denaturation at 94° C. for 5 min, denaturation at 98° C. for 10 seconds, annealing at 57° C. for 20 seconds and extension at 72° C. for 2 min. PCR products were detected by 1% agarose gel electrophoresis. The PCR products were recovered and ligated to pMD18T respectively for delivery to the company for sequencing. The LgE fragment and the RgE fragment with the correct sequencing results were digested with EcoRI, KpnI, BamHI and HindIII, respectively, and then ligated into the corresponding positions of the same enzyme-treated PUC18 plasmid to obtain the plasmid pUC18-LrgE containing LgE and RgE in turn.

Using the pMCherry-C1 plasmid as a template, the pMCherry-C1ΔMCS plasmid containing no multiple cloning sites was amplified by deleting the mutant pMCherry-C1 with the primers F-Mcherry and R-Mcherry. The PCR product was treated with DpnI enzyme to digest the template plasmid. i.e. the plasmid with MCS. The processed product is transformed directly into competent cells of TG1, picked monoclonal and then sent to the company for sequencing, sequencing to determine whether the deletion of the multiple cloning site (MCS). Using this modified correctly sequenced plasmid as a template, a complete Cherry expression cassette containing the promoter and SV40 tail was amplified using primers F-McherryCPS and P-McherryCPS. PCR products were detected by 1% agarose gel electrophoresis. The amplified Cherry expression cassette and PUC18-LrgE were double-digested with KpnI and BamHI, respectively, ligated and transformed into competent cells of TG1, and verified by sequencing, that is, the recombinant vector PUC18-gEloxpCherry was obtained, and the gE transfer vector plasmid was obtained.

Figure 8:
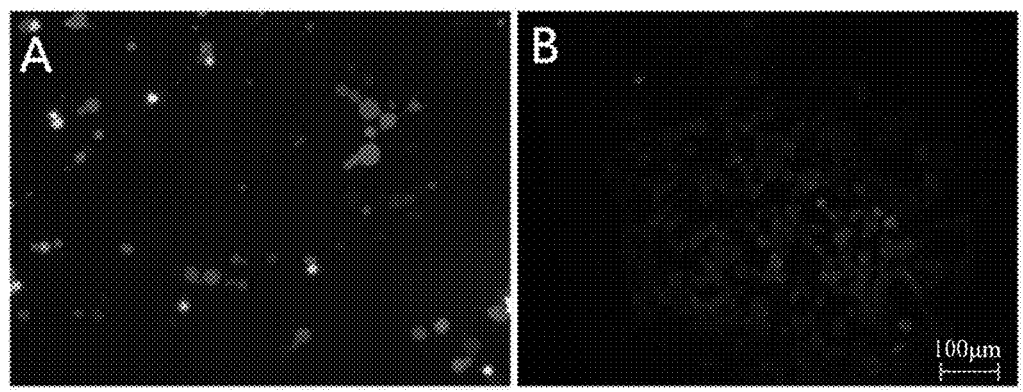
FIG. 8 is a fluorescence microscope observation of red fluorescence of recombinant virus on Vero cells, wherein A: two mixed viruses of PRV-DX and PRV-DX gE-/Cherry+; B: pure PRV-DX gE-/Cherry+.

The PUC18-gEloxpCherry transfer vector was about 6.3 kb in size (empty vector 2686 bp+LgE 1021 bp+CherryCPS 1704 bp+RgE 860 bp), as shown in FIG. 8, i.e., the resulting LgE, RgE and Cherry red fluorescent expression cassettes were PCR-Fragments according to their corresponding restriction sites, in turn connected to the corresponding position on PUC18 to obtain the vector, sent to the sequencing company correctly sequenced.

3. PRV-DX gE-Virus Construction

Figure 9:
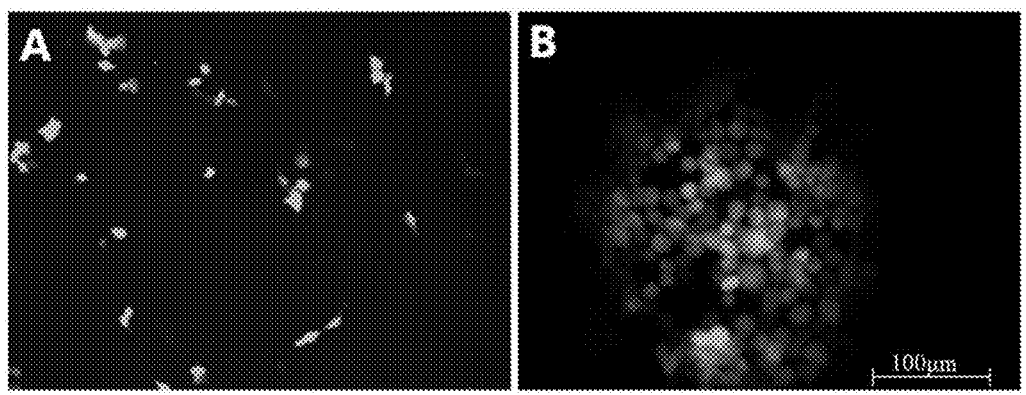
FIG. 9 is a fluorescence microscope observation of green fluorescence of recombinant virus on Vero cells, wherein A: two mixed virulence of PRV-DX gE- and PRV-DX gE-/TK-/EGFP; B: pure PRV-DX gE-/TK-/EGFP+ recombinant virus.

Liposomes lip2000 transfection reagent was used in transfection experiments. The specific operation in accordance with the instructions lip2000 is as follows: Taking six 2 mL EP tubes, marked 1 to 6, respectively, by adding 500 µL MEM medium and 10 µL lip2000, with a pipette blew evenly after standing 5 min; then taking the same six 6 EP tubes, also marked Nos. 1-6, each adding 500 µL MEM medium. Then, 1 µg of viral DNA and 3 µg of PUC18-gEloxpCherry plasmid were added to tubes 1 to 4, respectively. The tube No. 5 was added 1 µg of viral DNA as a single transfected virus DNA control. The tube No. 6 was added 3 µg PUC18-gEloxpCherry plasmid as a separate transfected plasmid control and mixed with a pipette. Each 500 µL MEM corresponding to the above markers was mixed. The mixture was allowed to rest at room temperature for 20 min. During the period, six-well plates covered with monolayer of Vero cells were discarded, and the medium was discarded and then washed twice with PBS. 1 mL of pre-treated mixture was added to each well and labeled. The plate was incubated at 37° C. incubator culture. After 5 hours, the medium containing transfection reagents were discarded and replaced with 2 mL of fresh medium containing 2% fetal bovine serum in each well. Then, the cell plate was incubated in a 37° C. incubator, and the cell changes in the co-transfected cells and the control transfected cells in the six-well plate were continuously observed. The co-transfected cells were harvested while the lesions and red fluorescence were harvested. That is, both the transfected DNA and the plasmid were expressed (FIG. 9A). At the same time, the cells transfected with plasmids only showed red fluorescence, and the cytopathic effect appeared only in cells transfected with parental DNA alone.

Under −70° C., the virus liquid was repeatedly frozen and thawed three times and inoculated on Vero cells covered with monolayer cells to be lesion, picking the red fluorescent lesions of the virus diluted by 10 times with dilution ratio of $10^1$-$10^{-6}$ to inoculate Vero cells covered with monolayers and incubated at 37° C. for 2 hours. Then all the supernatants were discarded, adding 1:1 mixture of 2×MEM (2% fetal bovine serum) and 2% low melting point agarose mixture, to be solidified and placed in a 37° C. incubator, observed for several days. When the cells appeared moderate red fluorescent plaques, the appropriate fluorescent plaques were picked and dissolved in 1 mL MEM medium, repeatedly frozen and thawed at −70° C. three times and then seeded in Vero cell monolayers for passage and plaque purification until The resulting clones of all diseased plaques showed red fluorescence, i.e., pure PRV-DX gE-/Cherry deletion mutants (FIG. 9B).

Genomic DNA of PRV-DX gE-/Cherry was extracted and treated with Cre recombinase at 37° C. for 2 hours. The treated product was extracted twice with Tris-saturated phenol, and the supernatant was extracted and then extracted twice with an equal volume of chloroform. The supernatant was aspirated, 2.5 times the volume of pre-cooled anhydrous ethanol was added at −70° C. for 1 hour to precipitate the DNA, and the precipitated DNA was washed with 75% ethanol. After the solution was dried and dissolved in TE, and the treated clean genomic DNA was obtained.

The above genomic DNA treated with Cre enzyme was transfected into Vero cells. When the medium was changed, a 1:1 mixture of 2×MEM (2% fetal bovine serum) and 2% low melting point agarose mixture were mixed and allowed to solidify Placed in 37° C. incubator, continuous observation for several days. When the lesion appeared, whether the diseased cells have red fluorescence was observed, and the non-fluorescent plaque was picked under the fluorescence microscope and then the plaque purification was performed, and repeated until all the lesions have no red fluorescence Pure PRV-DX gE-deletion mutants.

4. PRV-DX gE-Strain Identification and $TCID_{50}$ Determination

The DNA of the PRV-DX gE-deletion mutant was extracted and PCR was performed by using the primers gE-F and gE-R. Two controls were set up, one using PRV-DX strain parental DNA as a template and the other using PRV-DX gE-/Cherry DNA as a template. The PCR system is as follows: 2×GC buffer 12.5 μL, dNTPmix 2 μL, primer 1 μL each, template DNA 1 μL, PrimeSTAR enzyme 0.25 μL, and finally made up to 25 μL with water. The PCR reaction procedure was pre-denaturation at 94° C. for 5 min, denaturation at 98° C. for 10 seconds, annealing at 57° C. for 20 seconds and extension at 72° C. for 1 min 45 seconds. PCR products were detected by 1% agarose gel electrophoresis, sent to the company for sequencing verification. The results showed that the gE gene was indeed deleted by 1931 bp, leaving a loxp site. The result was in line with the theory that Cre recombinase cleaves the middle sequence and leaves a loxp site when there are two loxp sites in the DNA molecule that are aligned. The gE gene-deleted DX strain and DX parent strain respectively underwent $TCID_{50}$ determination. When the Vero cells in the 96-well plate were covered with a monolayer, the passaged cells were inoculated into a 96-well plate of 1 to 10 with a dilution ratio of 10-1 to 10-10 to 100 μL per well. The last two columns were added with equal volume of cell maintenance fluid as a negative control. 96 plates were cultured under 37° C. and in a 5% $CO_2$ incubator. The numbers of cytopathic holes were counted after 96 hours. The $TCID_{50}$ of virus was $10^{8.5}$ $TCID_{50}$/mL (gE gene deletion DX strain) by Reed-Muench method and $10^{8.6}$ $TCID_{50}$/mL (DX parent strain). This indicates that deletion of gE does not affect the virus proliferation on Vero cells.

5. Construction of TK Transfer Vector

The virus DNA of PRV-DX gE-single gene deletion strain was used as a template to amplify TK homologous recombination arm LTK and RTK with primers F-LTK and R-LTK, F-RTK and R-RTK. The PCR product was detected by 1% agarose gel electrophoresis, and the PCR product recovered was treated with rTaq enzyme plus poly A sticky end.

The above ligation products were transformed into TG1 competent cells, and the positive clones were picked and sent to Buo Shang Ltd. for sequencing. The LTK fragment and RTK fragment with the correct sequencing results were digested with EcoRI and KpnI, BamHI and HindIII, respectively, and ligated to the corresponding position of the same enzyme-treated PUC18 plasmid to obtain the plasmid PUC18-LRTK. The pEGFP-C2ΔMCS plasmid without multiple cloning sites was amplified by using the pEGFP-C2 plasmid as a template and the deletion mutation pEGFP-C2 with primers F-EGFP and R-EGFP. The PCR product was treated with DpnI enzyme to digest the template plasmid, i.e, the plasmid with MSC. The processed product was transformed directly into TG1, picked monoclonal and sent to the company for sequencing. A complete EGFP expression cassette containing the promoter and SV40 tail was amplified with primers F-EGFPCPS and P-EGFPCPS using the modified plasmid sequenced correctly as a template. PCR products were detected by 1% agarose gel electrophoresis. The amplified EGFP expression cassette and PUC18-LRTK were digested with KpnI and BamHI, respectively, and T4 ligase was ligated overnight at 16° C. The ligated product was transformed into TG1 and cultured in a 37° C. incubator. When its colonies appeared, the monoclonal antibody was picked for bacterial identification PCR. The bacterial PCR showed positive clones were sent to the company for sequencing identification. After sequencing, the recombinant vector PUC18-TkloxpEGFP was obtained and the strain was stored at −70° C. According to TIANGEN plasmid mini kit operation, PUC18-TKloxpEGFP plasmid DNA was extracted to obtain TK transfer vector DNA.

6. Construction of PRV-DX gE-/TK-Gene Deletion

Liposomes lip2000 transfection reagent was used to conduct transfection experiments. Six (6) autoclaved 2 mL centrifuge tubes were obtained, labeled 1 to 6, and were added to 500 μL DMEM medium and 10 μL lip2000, mixed well and then stood at room temperature for 5 min. Then another six (6) centrifuge tubes were obtained, similarly marked 1~6, and 500 μL DMEM medium were added. Then, 1 μg of PRV-DX/gE-gene-deleted viral genomic DNA and 3 μg of PUC18-TKloxpEGFP plasmid mixture were added to tubes Nos. 1 to 4. 1 μg of PRV-DX/gE gene-deleted virus genomic DNA was added into tube No. 5 as a single transfected virus DNA control. 3 μg of PUC18-TKloxpEGFP plasmid was added into tube No. 6 as a plasmid-independent control and mix well with a pipette tip. 500 μL of each of the DMEMs corresponding to the above marker were mixed and the mixture rested at room temperature for 20 min. For six-well plates covered with monolayer of Vero cells in six-well plate, the medium was discarded, washed twice with PBS spar. 1 mL of pretreated mixture was added into each well and labeled numbers 1 to 6, the cell plate placed under 37° C., and in a 5% $CO_2$ incubator. After 5 hours, the medium containing transfection reagents were discarded and replaced with 2 mL fresh medium containing 2% fetal bovine serum in each well. The cells were then incubated in a 5% $CO_2$ incubator at 37° C. The cells in the co-transfected wells of the six-well plate and the cells in the control transfected wells were continuously observed. When the co-transfected wells were infected with lesions and green fluorescence, the cells were harvested Virus liquid, which means that the transfected DNA and plasmid have been expressed.

Viral fluid was repeatedly frozen and thawed three times under −70° C. before inoculated on Vero cells. When lesions appeared in the cells, the green fluorescence of the lesion holes were picked, virus solution was harvested, vaccination Vero cells were diluted 10 times under the ratio of $10^{-1}$ to $10^{-6}$ and incubated for 2 hours at 37° C., then all supernatants were discarded. 1:1 mixture of 2×DMEM (2% fetal bovine serum) and 2% low melting point agarose were added. After solidification, it was placed in an incubator under 37° C. with 5% $CO^2$ for several days to observe the green fluorescent plaque. Fluorescent plaques were picked up and dissolved in 1 mL of DMEM medium. The cells were seeded repeatedly and plaque purified until all of the lesion plaques showed green fluorescence, i.e., pure PRV-DX gE-/TK-/EGFP+deletion mutants poison.

PRV-DX gE-/TK-/EGFP+ was seeded into small vials filled with monolayer Vero cells. When the cells appeared 80% lesions, genomic DNA was extracted and the concentration was determined, then treated with Cre recombinase at 37° C. for 2 hours, 200 ii L Tris-saturated phenol was extracted twice in the treated product system, and the supernatant was extracted twice with an equal volume of chloroform. The supernatant was obtained by aspiration, 2.5 times the volume of pre-cooled anhydrous ethanol was added for reaction for 1 hour at −70° C. to precipitate the DNA, and the precipitated DNA was washed with 75% ethanol. After the solution is dried and dissolved in TE, the treated clean genomic DNA is obtained.

The resulting DNA was PRV-DX gE-/TK-/EGFP+ and PRV-DX gE-/TK-two viral genomic DNA mixture since Cre enzyme was unable to 100% excise the Cherry gene. Genomic DNA previously treated with Cre enzyme was used to transfect Vero cells covered with monolayers as described above. When changing the medium, 2×DMEM (2% fetal bovine serum) and 2% low melting point agar Sugar mixture until it solidified and was placed in a 37° C., 5% $CO^2$ incubator, and was continuously observed for several days. When the lesion appeared, the diseased cells for green fluorescence was observed and the plaque without fluorescence was picked out, which is PRV-DX gE-/TK- recombinant virus, dissolved in 1 mL DMEM, freeze-thawed at −70° C., melted three times after inoculation with monolayer of Vero cells for plaque purification, so repeated until all the lesions plaque does not appear green fluorescence clone obtained is the PRV-DX gE-/TK-deficient virus.

7. PRV-DX gE-/TK-Strain Identification and Determination of the Virus $TCID_{50}$ Genomic DNA was extracted and PCR was performed using the primers TK623-F: GTTCGTAGAAGCGGTTGTGGCA (SEQ ID NO: 29) and TK623-R: CGTGTTGACCAGCATGGCGTAG (SEQ ID NO: 30). The upstream primer was located in the TK-deleted sequence, so that any band could not be amplified after TK was deleted. The parental strain of PRV-DX gE gene deletion DNA was used as a positive control. PCR products were detected by 1% agarose gel electrophoresis. The purified gE/TK double gene deletion virus was identified by TK gene primers, and the TK gene could not be detected. It was proved that the gE/TK gene was knocked out and the virulent PRV-DX gE/TK double gene deletion virus generation was obtained. The obtained gE/TK double gene deletion virus was named PRV-HD/c strain of PRV, and was deposited with the China General Microbiological Culture Collection Center of General Microbiology (No. 3 Beichen West Road, Chaoyang District, Beijing) (CGMCC) under the accession number of CGMCC No. 14325, and the storage time is Jul. 6, 2017.

The $TCID_{50}$ of gE/TK double gene deletion strain (PRV-HD/c strain), gE single gene deletion strain and DX parent strain were respectively measured in 96-well plates covered with monolayers of Vero cells. When the Vero cells in the 96-well plate were covered with a monolayer, the passaged cells were inoculated into a 96-well plate of 1-10 columns at a dilution of $10^{-1}$-$10^{-10}$ to 100 L per well. The last two columns were added with equal volume of cell maintenance fluid as a negative control. 96 plates were cultured in a 37° C., 5% $CO_2$ incubator, and the numbers of cytopathic holes were counted after 96 hours. The virus $TCID_{50}$ and gE/TK double gene deletion strains were calculated by Reed-Muench method (PRV-HD/c strain), gE single gene deletion strain and DX parent strain were $10^{8.6}$ $TCID_{50}$/mL, $10^{8.5}$ $TCID_{50}$/mL and $10^{8.6}$ $TCID_{50}$/mL, respectively, indicating that the deletion of the gE and TK genes did not affect the virus proliferation on Vero cells.

Example 7

1. Mice Pathogenicity Comparison

Experimental Methods: Seventy BALB/c mice aged 6 to 8 weeks were randomly divided into 7 groups of 10 rats. 1 to 3 groups were subcutaneously injected with 0.1 mL of virus solution of gE-/TK-double gene deletion strain (PRV-HD/c strain of PRV-HD/c strain) with $10^{6.0}$ $TCID_{50}$ subcutaneously in the back, 0.1 mL PRV-DX strain containing $10^{6.0}$ $TCID_{50}$ of parental virus, and the remaining one group was injected with 100 μL DMEM as a negative control group. After inoculation observation for 14 consecutive days, the clinical symptoms and death of mice were recorded.

As a result, the mice inoculated with $10^{6.0}$ $TCID_{50}$ PRV-DX strain developed apomorphism, loss of spirit and appetite, and inoculation site biting were observed at 48 hours after inoculation, and they all died within 72 hours. Mice vaccinated with the PRV-HD/c strain group showed no clinical signs of PRV and all survived during the experiment. This indicates that the deletion of gE and TK genes attenuates virulence and pathogenicity in mice.

2. Pig Pathogenicity Comparison

Experimental Methods: 15 PRV-negative, PRRSV-ELISA-negative, PRV-ELISA-negative 8-9-week-old breeding pigs were selected and pathogenicity comparison was conducted. The method of attack or challenge was as follows: 4 mL of each pig's nose was dripped, the feed after Co60 irradiation was fed, and the isolated pigs were fed by designated personnel. Body temperature was measured regularly every morning, and the anal swabs and nasal swabs were collected and immersed in 1 mL of PBS, respectively. Daily observation of the experimental pig mental state, appetite, health status and so on was conducted. Blood was collected from the anterior vena cava on days 0, 3, 7, 10 and 14 after challenge, and serum was separated.

As a result, all vaccinated pigs started to rise in body temperature on the first day after challenge with PRV-DX. On the second day, the body temperature of all vaccinated pigs was above 41° C., with depression and loss of appetite, and one pig had obvious symptoms. On the third day, the pigs in the challenge group all had fever over 41° C., one pig died, and the other four had obvious neurological symptoms. On the 4th day, all four died. For HD/c group, on the second day after inoculation, the body temperature of all vaccinated pigs increased slightly, and the body temperature lasted for 3 days. The body temperature of all pigs increased within 1° C., and their mental and appetite conditions were normal without any death. In the control group, 5 piglets from start to finish are very healthy, mandatory execution on the $14^{th}$ day. This indicated that the deletion of gE and TK attenuated the virulence and pathogenicity of pigs.

Example 8

1. Inactivated Vaccine Preparation and Testing

The virus solution (PRV-HD/c strain) with a titer of $10^{8.6}$ $TCID_{50}$/mL was slowly added with formaldehyde to a final concentration of 0.1% with stirring and inactivated by stirring at 37° C. for 48 hours. Vero cell monolayers were inoculated with the inactivated virus solution and harvested at 37° C. in a 5% $CO_2$ incubator for 72 hours. Blotting was performed 3 times blindly, and no cytopathic effect was determined as inactivation test. The qualified venom was mixed with ISA adjuvant at a ratio of 3:1 (v/v), and emulsified to prepare the oil-in-water PRV-HD/c strain inactivated vaccine.

2. Mouse Immunogenicity Test

A total of 20 SPF mice aged 5~6 weeks were randomly divided into 2 groups with 10 mice in each group. One group received intraperitoneal injections of 0.2 mL of PRV-HD/c inactivated vaccine with an antigenic level of $10^{8.6}$ $TCID_{50}$/mL before inoculation. One group was intraperitoneally inoculated with 0.2 mL of DMEM as a negative control. The challenge was then challenged with PRV-DX virulent strain with a $TCID_{50}$ value of $10^{6.6}$ $TCID_{50}$/mL 21 days after immunization at the dose of 0.1 mL subcutaneously. The mice were observed after the clinical symptoms of poisoning, and the number of deaths in mice was calculated.

Results: After immunization of mice with different antigen content, the mice were in good mental state and normal appetite. There was no difference with the control, indicating that the vaccine had no side effects on the mice. After challenge, the non-immune control group began to have obvious pseudorabies symptoms 72 hours after onset, such as apathetic, rough hair disorder, loss of appetite, weight loss, and constantly biting vaccination sites. Vaccine immunized group did not show clinical symptoms. After continuous observation for 14 days, the mortality rate of mice in non-immune challenge group was 90% and survival rate was 10%. The survival rate of mice in vaccination group was 90% and mortality rate was 10%. The results showed that PRV-HD/c inactivated vaccine produced 90% protection efficiency in mice when the antigen content was $10^{8.6}TCID_{50}$/mL.

3. Pig Immunogenicity Test

Ten 14-day-old crossbred pigs that were negative for PRV, negative for PRRSV-ELISA and negative for PRV-ELISA were selected for this experiment. The pigs were randomly divided into 2 groups with 5 pigs in each group. The first group was intramuscularly inoculated with PRV-HD/c inactivated vaccine with an antigenic level of $10^{8.6}$ $TCID_{50}$/mL before inactivation, 2 mL/pig; the second group was not injected with the vaccine as blank control group (frozen cell lysate). Each group was isolated for feeding. The changes of body temperature after immunization were observed. PRV antibody was detected in the sera of 7-21 days after immunization. 21 days after immunization with PRV-DX virulent strain of $10^{4.87}TCID_{50}$/mL were challenged at a dose of 4 mL per pig intranasal injection to observe the clinical symptoms and death of immunized pigs, the death of pigs and on the 14th day, the animals were sacrificed to dissect the organs and tissues such as the brain, tonsils, lungs, spleen and inguinal lymph nodes of the animals and to observe the ocular and pathological changes. Serum and nasal, anal swabs and tissue samples were collected 7 to 14 days after challenge and the copy number of PRV virus nucleic acid and the PRV virus were determined.

The experimental pigs were observed for 21 days after immunization. The pigs in each immunized group and the control group showed good mental state and normal appetite. Except for a slight increase in body temperature after 24 hours of immunization, After 14 days of challenge, the body temperature of the non-immune control group began to rise on the second day after the challenge, and sustained high temperature for more than 3 days. All the pigs without vaccine vaccination died on the 7th day after the challenge and the mortality rate was 100%. 3 to 5 days after inoculation, there was a transient increase in body temperature of pigs vaccinated with inactivated vaccine, but no pigs died, the survival rate of 100%. The results showed that PRV-HD/c inactivated vaccine could produce 100% immunepotency on 14-21 day-old piglets when the antigen content was $10^{8.6}TCID_{50}$/mL.

The above test results show that the inactivated vaccine prepared by the PRV-HD/c virus obtained in the present invention has good immune-protective effect on mice and pigs and has strong immunogenicity.

Example 9

Sixty five-to-six-week-old SPF mice were randomly divided into 6 groups of 10 pigs, two of which were vaccinated with the PRV-HD/c strain inactivated vaccine prepared in Example 8, and two groups were vaccinated with commercially available PRV inactivated vaccine A, two groups were vaccinated with DMEM control, inoculation dose was 0.2 ml/each. The method of inoculation was intraperitoneal injection. Twenty-one days after immunization, these mice were challenged with the virulent PRV-DX strain or PRV-SC classical strains at a dose of 0.1 ml ($10^{5-6}TCID_{50}$/0.1 ml), respectively, and the mice were observed for clinical symptoms after 14 days of challenge and statistics the number of mice in each group.

Results: The mice were in good mental state and normal appetite after inoculation of different immunogens. There was no difference with the control group, indicating that the vaccine prepared in Example 8 of the present invention and the commercial vaccine were safe to mice. For the group with PRV HD/c inactivated vaccine, at 21 days after immunization, the mice were inoculated with virulent PRV-DX strain or PRV-SC classical virus at a dose of 0.1 ml ($10^{5.6}TCID_{50}$/0.1 ml). After 14 days post-inoculation, the survival rates of mice were both 100%. For commercial PRV vaccine immunized mice group A, at 21 days after immunization the mice were inoculated with PRV-DX and PRV-SC strain at a dose of 0.1 ml ($10^{5.6}TCID_{50}$/0.1 ml), and the survival rates of mice were 80% and 90% respectively. The control group was also treated with PRV-DX strain and PRV-SC strain of attack at a dose of 0.1 ml ($10^{5.6}TCID_{50}$/0.1 ml), the survival rates were 0. The result shows that the PRV HD/c inactivated vaccine has a good protective effect on mice, which can resist the absolute lethal dose of newly domestic and classic strains of PRV to cross-protect, and the PRV HD/c inactivated vaccines in mice immunoprotective effect is better than the commercial PRV inactivated vaccine A.

Example 10

120 SPF mice aged 5~6 weeks were randomly divided into 12 groups, 10 mice in each group. The three groups were inoculated intraperitoneally with 0.1 ml ($10^{7.0}$ $TCID_{50}$/0.1 ml) of PRV-HD/c virus solution, and the three groups were inoculated with 0.1 ml ($10^{6.0}$ $TCID_{50}$/0.1 ml) of PRV-HD/c virus solution, three groups inoculated with 0.1 mL ($10^{5.0}$ $TCID_{50}$/0.1 ml) of PRV-HD/c virus solution, three groups were inoculated with virus DMEM as a control. At 4 days, 7 days, and 10 days after vaccination, these mice were inoculated with virulent PRV-DX strain at 0.1 ml ($10^{5.6}$ $TCID_{50}$/0.1 ml) and were observed for 14 days.

Results: After being inoculated with PRV-HD/c with different antigen levels, the mice were in good mental state, with normal appetite and no clinical symptoms. There was no difference with the control, indicating that PRV-HD/c attenuated mice without side effects. Mice inoculated with PRV-DX strain on day 4 post challenge showed that more than 80% of deaths occurred in mice vaccinated with attenuated live vaccine of different antigen content on day 4, 7 days after vaccination. 7 days after immunization, PRV-DX was inoculated, the antigen concentration was $10^{5.0}$ TCID$_{50}$ attenuated live vaccine group, the protection rate of mice was 20%. The antigen concentration was $10^{6.0}$ TCID$_{50}$ for attenuated live vaccine group, the protection rate of mice was 40%. The antigen concentration was $10^{7.0}$ TCID$_{50}$ for attenuated live vaccine group, the protection rate of mice was 70%. On the 10th day after vaccination, the virus was inoculated with PRV-DX strain, the protection rate was 50% in $10^{5.0}$ TCID$_{50}$ attenuated live vaccine group, and the antigen content $10^{6.0}$ TCID$_{50}$ minus toxic vaccine group, mouse protection rate was 40%, the antigen content $10^{7.0}$ TCID$_{50}$ live attenuated vaccine group, the protection rate of mice was 90%; the mortality rate of mice in control group was above 100%. The results showed that the protective effect of PRV-HD/c attenuated live vaccine was not found 4 days after immunization, and the protective effect on mice 7 days after immunization did not reach the ideal level. But the challenge was again 10 days after immunization, the $10^{7}$TCID$_{50}$ immunized mice survived up to 90%, after being challenged with PRV-DX strain.

The above test results show that the attenuated live vaccine prepared with the PRV-HD/c virus strain obtained in the present invention has a good immune-protective effect on mice when the antigen content reaches $10^{6.0}$ TCID$_{50}$/mL for 14 days after the immunization, with strong immunogenicity.

The invention claimed is:

1. An attenuated strain of pseudorabies virus with gE/TK double-deletion, which is named as PRV-HD/c strain of porcine pseudorabies virus Type II, and has an accession number of CGMCC No. 14325.

2. The method for preparing the attenuated strain of pseudorabies virus according to claim 1, characterized in that it comprises the following steps:
   (1) isolating a wild-type pseudorabies virus type II strain, which is named as PRV-DX, and the accession number was CGMCC No. 14326;
   (2) obtaining a pseudorabies virus attenuated strain was obtained by virus rescue after knockdown of both gE and TK genes in the genome of PRV-DX strain.

3. A method of using the attenuated PRV strain as claimed in claim 1 in the preparation of a pseudorabies vaccine, the method comprising the following steps:
   adding formaldehyde to the attenuated PRV strain to obtain a virus solution with a concentration of 0.1% (v/v);
   inactivating the virus solution by stirring at 37° C. for 48 hours;

inoculating vero cell monolayers with the inactivated virus solution at 37° C. in a 5% $CO_2$ incubator for 72 hours and harvesting;

performing blotting 3 times blindly, and determining that venom is qualified when no cytopathic effect is found; and mixing the qualified venom with ISA adjuvant at a ratio of 3:1 (v/v), and emulsifying to prepare the oil-in-water PRV-HD/c strain inactivated vaccine.

4. The method according to claim 3, characterized in that an immune object of the pseudorabies vaccine is a pseudorabies virus susceptible animal.

5. The method according to claim 4, wherein the pseudorabies virus susceptible animal is a pig or a mouse.

6. An inactivated vaccine against pseudorabies disease, comprising an inactivated attenuated strain of pseudorabies virus according to claim 1.

7. A live attenuated pseudorabies vaccine, comprising the attenuated strain of pseudorabies virus according to claim 1.

* * * * *

SEQUENCE LISTING

<160> NUMBER OF SEQ ID NOS: 37

<210> SEQ ID NO 1
<211> LENGTH: 19
<212> TYPE: DNA
<213> ORGANISM: Artificial Sequence
<220> FEATURE:
<223> OTHER INFORMATION: Synthesized

<400> SEQUENCE: 1
cggcaagtgc gtctccaag                                         19

<210> SEQ ID NO 2
<211> LENGTH: 20
<212> TYPE: DNA
<213> ORGANISM: Artificial Sequence
<220> FEATURE:
<223> OTHER INFORMATION: Synthesized

<400> SEQUENCE: 2
agggcgaagg agtcgtaggg                                        20

<210> SEQ ID NO 3
<211> LENGTH: 19
<212> TYPE: DNA
<213> ORGANISM: Artificial Sequence
<220> FEATURE:
<223> OTHER INFORMATION: Synthesized

<400> SEQUENCE: 3
gctctgcgtg ctgtgctcc                                         19

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
tcgtcacttc cggtttctcc                                        20

<210> SEQ ID NO 5
<211> LENGTH: 23
<212> TYPE: DNA
<213> ORGANISM: Artificial Sequence
<220> FEATURE:
<223> OTHER INFORMATION: Synthesized

```
<400> SEQUENCE: 5
ttttatctcc gtccgcgccg ttt                                         23

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
ctcgctgtag tagcagtccg agt                                         23

<210> SEQ ID NO 7
<211> LENGTH: 25
<212> TYPE: DNA
<213> ORGANISM: Artificial Sequence
<220> FEATURE:
<223> OTHER INFORMATION: Synthesized

<400> SEQUENCE: 7
acagggcgtc ggggtcctcg ctctc                                       25

<210> SEQ ID NO 8
<211> LENGTH: 18
<212> TYPE: DNA
<213> ORGANISM: Artificial Sequence
<220> FEATURE:
<223> OTHER INFORMATION: Synthesized

<400> SEQUENCE: 8
cgaggcgtca tgcccgct                                               18

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
ccgtcgccat gtgtgccact                                             20

<210> SEQ ID NO 10
<211> LENGTH: 19
<212> TYPE: DNA
<213> ORGANISM: Artificial Sequence
<220> FEATURE:
<223> OTHER INFORMATION: Synthesized

<400> SEQUENCE: 10
acaaacaacc ggacgcgat                                              19

<210> SEQ ID NO 11
<211> LENGTH: 21
<212> TYPE: DNA
<213> ORGANISM: Artificial Sequence
<220> FEATURE:
<223> OTHER INFORMATION: Synthesized

<400> SEQUENCE: 11
gggtcaagga cgccttctta a                                           21

<210> SEQ ID NO 12
<211> LENGTH: 21
```

<212> TYPE: DNA
<213> ORGANISM: Artificial Sequence
<220> FEATURE:
<223> OTHER INFORMATION: Synthesized

<400> SEQUENCE: 12
ggcacggcaa actttattgg g                                              21

<210> SEQ ID NO 13
<211> LENGTH: 26
<212> TYPE: DNA
<213> ORGANISM: Artificial Sequence
<220> FEATURE:
<223> OTHER INFORMATION: Synthesized

<400> SEQUENCE: 13
cggaattcga cgatagacgg gacgct                                         26

<210> SEQ ID NO 14
<211> LENGTH: 26
<212> TYPE: DNA
<213> ORGANISM: Artificial Sequence
<220> FEATURE:
<223> OTHER INFORMATION: Synthesized

<400> SEQUENCE: 14
ggggtaccgg gtgcccaggt ttaaaa                                         26

<210> SEQ ID NO 15
<211> LENGTH: 31
<212> TYPE: DNA
<213> ORGANISM: Artificial Sequence
<220> FEATURE:
<223> OTHER INFORMATION: Synthesized

<400> SEQUENCE: 15
acgcgtcgac caggacgact cggactgcta c                                   31

<210> SEQ ID NO 16
<211> LENGTH: 30
<212> TYPE: DNA
<213> ORGANISM: Artificial Sequence
<220> FEATURE:
<223> OTHER INFORMATION: Synthesized

<400> SEQUENCE: 16
cccaagcttg ttcaggacgg acgaccactc                                     30

<210> SEQ ID NO 17
<211> LENGTH: 30
<212> TYPE: DNA
<213> ORGANISM: Artificial Sequence
<220> FEATURE:
<223> OTHER INFORMATION: Synthesized

<400> SEQUENCE: 17
tacaagtccg gactcggatc tagataactg                                     30

<210> SEQ ID NO 18
<211> LENGTH: 30
<212> TYPE: DNA
<213> ORGANISM: Artificial Sequence
<220> FEATURE:
<223> OTHER INFORMATION: Synthesized

<400> SEQUENCE: 18
cagttatcta gatccgagtc cggacttgta                                          30

<210> SEQ ID NO 19
<211> LENGTH: 62
<212> TYPE: DNA
<213> ORGANISM: Artificial Sequence
<220> FEATURE:
<223> OTHER INFORMATION: Synthesized

<400> SEQUENCE: 19
ggggtaccat aacttcgtat aatgtatgct atacgaagtt attagttatt aatagtaatc       60
aa                                                                      62

<210> SEQ ID NO 20
<211> LENGTH: 62
<212> TYPE: DNA
<213> ORGANISM: Artificial Sequence
<220> FEATURE:
<223> OTHER INFORMATION: Synthesized

<400> SEQUENCE: 20
cgggatccat aacttcgtat agcatacatt atacgaagtt atgatgagtt tggacaaacc       60
ac                                                                      62

<210> SEQ ID NO 21
<211> LENGTH: 26
<212> TYPE: DNA
<213> ORGANISM: Artificial Sequence
<220> FEATURE:
<223> OTHER INFORMATION: Synthesized

<400> SEQUENCE: 21
cggaattcat cctccggatc tacctc                                            26

<210> SEQ ID NO 22
<211> LENGTH: 26
<212> TYPE: DNA
<213> ORGANISM: Artificial Sequence
<220> FEATURE:
<223> OTHER INFORMATION: Synthesized

<400> SEQUENCE: 22
ggggtaccag cgaggccacc accagg                                            26

<210> SEQ ID NO 23
<211> LENGTH: 26
<212> TYPE: DNA
<213> ORGANISM: Artificial Sequence
<220> FEATURE:
<223> OTHER INFORMATION: Synthesized

<400> SEQUENCE: 23
cgggatccat ggacgcgctc gtggcc                                            26

<210> SEQ ID NO 24
<211> LENGTH: 27
<212> TYPE: DNA
<213> ORGANISM: Artificial Sequence
<220> FEATURE:
<223> OTHER INFORMATION: Synthesized

<400> SEQUENCE: 24
cccaagctta gctggaagac gaaccac                                           27

```
<210> SEQ ID NO 25
<211> LENGTH: 33
<212> TYPE: DNA
<213> ORGANISM: Artificial Sequence
<220> FEATURE:
<223> OTHER INFORMATION: Synthesized

<400> SEQUENCE: 25
ggggtaccaa tagtaatcaa ttacggggtc att                                    33

<210> SEQ ID NO 26
<211> LENGTH: 26
<212> TYPE: DNA
<213> ORGANISM: Artificial Sequence
<220> FEATURE:
<223> OTHER INFORMATION: Synthesized

<400> SEQUENCE: 26
cgggatccag atacattgat gagttt                                            26

<210> SEQ ID NO 27
<211> LENGTH: 67
<212> TYPE: DNA
<213> ORGANISM: Artificial Sequence
<220> FEATURE:
<223> OTHER INFORMATION: Synthesized

<400> SEQUENCE: 27
ggggtaccat aacttcgtat aatgtatgct atacgaagtt ataatagtaa tcaattacgg       60
ggtcatt                                                                 67

<210> SEQ ID NO 28
<211> LENGTH: 60
<212> TYPE: DNA
<213> ORGANISM: Artificial Sequence
<220> FEATURE:
<223> OTHER INFORMATION: Synthesized

<400> SEQUENCE: 28
cgggatccat aacttcgtat agcatacatt atacgaagtt atagatacat tgatgagttt       60

<210> SEQ ID NO 29
<211> LENGTH: 22
<212> TYPE: DNA
<213> ORGANISM: Artificial Sequence
<220> FEATURE:
<223> OTHER INFORMATION: Synthesized

<400> SEQUENCE: 29
gttcgtagaa gcggttgtgg ca                                                22

<210> SEQ ID NO 30
<211> LENGTH: 22
<212> TYPE: DNA
<213> ORGANISM: Artificial Sequence
<220> FEATURE:
<223> OTHER INFORMATION: Synthesized

<400> SEQUENCE: 30
cgtgttgacc agcatggcgt ag                                                22

<210> SEQ ID NO 31
<211> LENGTH: 2745
<212> TYPE: DNA
<213> ORGANISM: Pseudorabies virus strain PRV-DX
```

<400> SEQUENCE: 31

```
ctaggggcg tcggggtcct cgttctcgag gcgctggtag tgccggcggc gcgtggccat      60
cgccccgacg cggctggcca gcagcgcggg cccgctgttc ttcttgcgcg ccttgtgctc     120
ctgctgctcg agggccgaca cgatggacat gtaccggatc atgtcccggg cctggtccag    180
cttggcctcg tccacgtcgt cctcttcgac gccgtcctcc ttgagcgcct tcgtcgtgac    240
ggggtacagg gccttcatgg ggttgcggcg caggcgcgag atgtgccggt aggccaggaa    300
ggccgcgacc aggccggcca gcaccagcag cccgatggcg agcgccccga aggggttgga    360
caggaaggac accatgccgc cgacggccga gatcacggcc ccgtggcgc ccaggaccac     420
cttgccgacg gcggcgccca cgtcgccgag gccctggaag aagttggcga tgccgcgcag    480
cagcaccacg ttgtggtcca ccttgaccac gcggtcaatg tcgtagaact tgagcgcgtg    540
cagctggttg cggcgctgga tctcgctgta gtccaggagg cccgtgtcgg cgagctcctc    600
gcgcgtgtac acctcgaggg gcaggaactc gcggtcctcg agcagcgtca ggttcagggt    660
cacccgcgtg ctgatcgtct cgggcacctc caccatgcgc acgtagctgt agtcctcgta    720
gtacacgtac ccgccgccca gcttaaagta gcgccggtgg ttgccggtgc agggctcgat    780
gaggtcgcgc gagatgagga gctcgttgtc gtcgccgagc tggccctcga tcacgcccgt    840
gccgttgtgc tcgaaggtca ccagcgggcg gctgtagcac gtgccgcgct cgccgggcac    900
gcgcatggag ttctgcacgt acacgccgcc gcgcacctcc acgcaccgcg agatggccat    960
cacgtcgccg agcatgcgcg ccgagacgcg ctggcccagc gcggccgtgg ccacggcgct   1020
ggggttcagg cgcgacatct cgccccacag ggtgcggtcc ttgttctgca gctcgcacca   1080
ggcggccgcg atgcggctca gcatgtcgtt cacgtgcgcc tggatgtggt cgtaggtgaa   1140
ctgcaggcgc gcaaactcgg ccgagcccgt ggtgatgcgc aggtgccccg tgccgttgac   1200
ggccggcggc tcgggcgtcc ccgccgggcc ggggagcgc cgggcccgac gggcggccgc    1260
ggggacgcg gggcccacga cgccggcgag gccgaggcgc tcgagctcgc gcgcgtacag    1320
ctgcgccagc tcgttcgaga tcagcgggcg gaaggccacc acgaagcccc cgcgggcgag   1380
gtacacctcg ggcttgtcgc cggccagcac gtgcgtgttg ttgtagcgcc gccggtagat   1440
ggcgtcgatg gcctccgagg cctcgcggag gacgcagtcg cccaggtgca cgcgctgcag   1500
gtcgagctgc gtgacgtcgc tgacgaagga ggcgcccagg gccgcgacg tgaagcggaa    1560
ggacccgtcg cgcgtctcgt cgcggatcat ctcctcggcc tcgcgccact tggccaggct   1620
gcacacgcgc cgcgtcttgg gggcccagtc ccaggccacc gtgaagtgcg gcgtgcgcag   1680
aaagttgcgc gtcacgctct cggaggcgcg gaggcgcgag tccaggtcga tggggtagta   1740
gtgctccacc tgctggaagc gcccgggcgc gtagccgatg tgctcccgt gggcccctc     1800
gcgcaggccg tagaagggg acatgtacat gatgtccccc gtggacaggg cgaaggagtc    1860
gtaggggtac acgagcgcg cctccacctc ctcgacgatg cagttgacgg aggtgcccgt    1920
gtggtagaag cccgcggcgc cgatcttggt gtaggtgtcg ttggtggtgt gccagccgcg   1980
ggtgccgagc gcgttcaggc gcgaggggcg caggtccacc tcgacggggt tctcgtcgcg   2040
gtcgaaggcg gtcaccttgt ggttgttgcg cacgtactcg gccttggaga cgcacttgcc   2100
gcggcggtcg atcacgtccg tgatctcctg cacggggacg ggcacgcggt ccgtgaagcg   2160
gttcgtgatg gccgcgtacg tgctcccgga ccacacggtc gtgacgatga cgttcttgta   2220
gtagatgtgg gccttgaact tgtgcggggc gatgttctcc ttgaagagca cggcgatccc   2280
ctccgtgaag ttgcgcccct gcgagtactc ggggcaggcc tgctcgggct ccaggcgcac   2340
```

```
caccgtggag ccggacggcg gcgggcagac gtagaagcgg tcccgctcgg tcgcggccgc    2400
gcgcacggcc gtgcgcgcgt ccaggtcgcc gtactcgccg tcgggggcgt ccagggggcc    2460
gggggagacg gccccgtcga tctcctcgag ggactcctcc gcggagaagc cgtctggggt    2520
ggcgcccgtc ccggggcgcgg gcgaggccga ggcggcccgc gtcacggccg ccgcgccgca    2580
cgtcggggtc gcggcgagcg ccagcagcag cagcgctagc gcgacggcgc cccgcgcagc    2640
tgcagcgtgg tgtggagcag gccaaagacg tccgaggcca gcaccgccgt ggtgcccggg    2700
ccgatgcccg cggggcccgc gccaaagacc gccaccagcg ggcat                     2745
```

<210> SEQ ID NO 32
<211> LENGTH: 1464
<212> TYPE: DNA
<213> ORGANISM: Pseudorabies virus strain PRV-DX

<400> SEQUENCE: 32

```
atggcctcgc tcgcgcgtgc gatgctcgcg ctgctggcgc tctacacggc ggccatcgcc      60
gcggcgccgt cgtccacgac ggcgctcggc acgacgccca cgggggcgg gggcggcaac     120 agcagcgcgg gcgagctctc gccctcgccg ccctcgacgc ccgagcccgt ctcggggacg     180 acggggggccg cggcctccac gcccgccgcc gtctcgacgc cccgggtccc gccgccctcg     240
gtctcgcgcc ggaagcccca gcggaacggg aacaggacgc gcgtccacgg cgacaaggcc     300
acctcgcacg ggcgcaagcg catcgtgtgc cgcgagcggc tgttctcggc gagggtgggg     360
gacgcggtca gcttcgggtg cgccgtcgtc ccgcgcgccg gggagacctt cgaggtccgc     420
ttctgccgcc gcgggcgctt ccgctcgccc gacgccgacc ccgagtactt tgacgagccc     480
ccgcgcccgg agctcccgcg ggagcggctc ctcttcagct ccgccaacgc ctccctcgcc     540
cacgcggacg cgctcgcctc cgccgtcgtc gtcgagggcg agcgcgcgac cgtcgccaac     600
gtctcgggcg aggtgtccgt gcgcgtggcc gggcggacg ccgagaccga gggcgtctac     660
acgtggcgcg tgctgtccgc caacggcacc gaggtccgca gcgccaacgt ctcgctcgtc     720
ctgtaccacc agcccgagtt cggcctgagc gcgccgcccg tcctcttcgg cgagcccttc     780
cgggcggtgt gcgtcgtccg cgactactac ccgcggcgca gcgtgcgcct gcgctggttc     840
gcggacgagc acccggtgga cgccgccttc gtgaccaaca gcaccgtggc cgacgagctc     900
gggcgccgca cgcgcgtctc cgtggtgaac gtgacgcgcg cggacgtccc gggcctcgcg     960
gccgcggacg acgcggacgc gctcgcgccg agcctgcgct gcgaggccgt gtggtaccgc    1020
gacagcgtgg cctcgcagcg cttctccgag gccctgcgcc ccacgtcta ccaccccggcg    1080 gcggtctcgg tgcgcttcgt cgagggcttc gccgtctgcg acggcctctg cgtgcccccg    1140
gaggcgcgcc tcgcctggtc cgaccacgcc gccgacaccg tctaccacct cggcgcctgc    1200
gccgagcacc ccggcctgct caacgtgcgg agcgcccgcc cgctgtcgga cctcgacggg    1260
cccgtcgact acacctgccg cctcgagggc atgcccctcgc agctgcccat cttcgaggac    1320
acgcagcgct acgacgcctc ccccacgtcc gtgagctggc ccgtcgtgac cagcatgatc    1380
accgtcatcg ccggcatcgc catcctagcc atcgtgctgg tcatcatggc gacgtgcgtc    1440
tactaccgcc ggtccgcgct gtga                                           1464
```

<210> SEQ ID NO 33
<211> LENGTH: 1902
<212> TYPE: DNA
<213> ORGANISM: Pseudorabies virus strain PRV-DX

<400> SEQUENCE: 33

```
gcacacaccg gggttgagac catgcggccc tttctgctgc gcgccgcgca gctcctggcg      60
ctgctggccc tggcgctctc caccgaggcc ccgagcctct ccgccgagac daccccgggc     120
cccgtcaccg aggtcccgag tccctcggcc gaggtctggg acgacctctc caccgaggcc     180
gacgacgatg acctcaacgg cgacctcgac ggcgacgacc gccgcgcggg cttcggctcg     240
gccctcgcat ccctgaggga ggcgccccgg gcccatctgg tgaacgtgtc cgagggcgcc     300
aacttcaccc tcgacgcgcg cggcgacggc gccgtgctgg ccgggatctg gacgttcctg     360
cccgtccgcg gctgcgacgc cgtgtcggtg accacggtgt gcttcgagac cgcgtgccac     420
ccggacctgg tgctgggccg cgcctgcgtc cccgaggccc ggagatgggg catcggcgac     480
tacctgccgc ccgaggtgcc gcggctccgg cgcgagccgc ccatcgtcac cccggagcgg     540
tggtcgccgc acctgagcgt cctgcgggcc acgcccaacg acacgggcct ctacacgctg     600
cacgacgcct cggggccgcg ggccgtgttc tttgtggcgg tgggcgaccg gccgcccgcg     660
ccggcggacc cggtgggccc cgcgcgccac gagccccgct ccacgcgct cggcttccac      720
tcgcagctct tctcgcccgg ggacacgttc gacctgatgc cgcgcgtggt ctcggacatg     780
ggcgactcgc gcgagaactt taccgccacg ctggactggt actacgcgcg cgcgcccccg     840
cggtgcctgc tgtactacgt gtacgagccc tgcatctacc accgcgcgc gcccgagtgc      900
ctgcgcccgg tggaccccgg cgtgcagctt cacctcgccgg cgcgcgcgcg gctggtggcg    960
cgccgcgcgt acgcctcgtg cagcccgctg ctcggggacc ggtggctgac cgcctgcccc    1020
ttcgacgcct tcggcgagga ggtgcacacg aacgccaccg cggacgagtc ggggctgtac    1080
gtgctcgtga tgacccacaa cggccacgtc gccacctggg actacacgct cgtcgccacc    1140
gcggccgagt acgtcacggt catcaaggag ctgacggccc cggcccgggc ccgggcacc     1200
ccgtggggcc ccggcggcgg cgacgacgcg atctacgtgg acggcgtcac gacgccggcg    1260
ccgcccgcgc gcccgtggaa cccgtacggc cggacgacgc ccgggcggct gtttgtgctg    1320
gcgctgggct ccttcgtgat gacgtgcgtc gtcgggggg ccatctggct ctgcgtgctg     1380
tgctccggc gccgggcggc ctcgcggccg ttccgggtgc cgacgcgggc gcggacgcac    1440
atgctctctc cggtgtacac cagcctgccc acgcacgagg actactacga cggcgacgac    1500
gacgacgacg aggaggcggg cgtcatccgc cggcggcccg cctcccccag cggagacagc    1560
ggctacgagg ggccgtacgc gagcctggac cccgaggacg agttcagcag cgacgaggac    1620
gacgggctgt acgtgcgccc cgaggaggcg ccccgctccg gcttcgacgt ctggttccgc    1680
gatccggaga aaccggaagt gacgaatgga cccaactatg gcgtgaccgc caaccgcctg    1740
ttgatgtccc gccccgctta aataccggga gaaccggtcc gccgcattc cgacatgccc     1800
ggcgccgcct ccgtcgacat ggacacgttt gaccccagcg ccccgtccc gacgagcgtc     1860
tcgaacccgg ccgccgacgt cctgctggcc cccaaggacc cc                       1902
```

<210> SEQ ID NO 34
<211> LENGTH: 963
<212> TYPE: DNA
<213> ORGANISM: Pseudorabies virus strain PRV-DX

<400> SEQUENCE: 34

```
atgcgcatcc tccggatcta cctcgacggc gcctacggca ccggcaagag caccacggcc      60
cgggtgatgg cgctcggcgg ggcgctgtac gtgcccgagc cgatggcgta ctggcgcact     120
ctgttcgaca cggacacggt ggccggtatt tacgatgcgc agacccggaa gcagaacggc     180
```

```
agcctgagcg aggaggacgc ggccctcgtc acggcgcagc accaggccgc cttcgcgacg      240
ccgtacctgc tgctgcacac gcgcctggtc ccgctcttcg ggcccgcggt cgagggcccg      300
cccgagatga cggtcgtctt tgaccgccac ccggtggccg cgacggtgtg cttcccgctg      360
gcgcgcttca tcgtcgggga catcagcgcg gcggccttcg tgggcctggc ggccacgctg      420
cccggggagc cccccggcgg caacctggtg gtggcctcgc tggacccgga cgagcacctg      480
cggcgcctgc gcgcccgcgc gcgcgccggg gagcacgtgg acgcgcgcct gctcacggcc      540
ctgcgcaacg tctacgccat gctggtcaac acgtcgcgct acctgagctc ggggcgccgc      600
tggcgcgacg actgggggcg cgcgccgcgc ttcgaccaga ccgtgcgcga ctgcctcgcg      660
ctcaacgagc tctgccgccc gcgcgacgac cccgagctcc aggacaccct cttcggcgcg      720
tacaaggcgc ccgagctctg cgaccggcgc gggcgcccgc tcgaggtgca cgcgtgggcg      780
atggacgcgc tcgtggccaa gctgctgccg ctgcgcgtct ccaccgtcga cctggggccc      840
tcgccgcgcg tctgcgccgc ggccgtggcg gcgcaggcgc gcggcatgga ggtgacggag      900
tccgcgtacg gcgaccacat ccggcagtgc gtgtgcgcct tcacgtcgga gatgggggtg      960
tga                                                                   963

<210> SEQ ID NO 35
<211> LENGTH: 17
<212> TYPE: DNA
<213> ORGANISM: Artificial Sequence
<220> FEATURE:
<223> OTHER INFORMATION: Synthesized

<400> SEQUENCE: 35
cacgccgatg tggtgga                                                     17

<210> SEQ ID NO 36
<211> LENGTH: 19
<212> TYPE: DNA
<213> ORGANISM: Artificial Sequence
<220> FEATURE:
<223> OTHER INFORMATION: Synthesized

<400> SEQUENCE: 36
ggtactggcc ctcgttgaa                                                   19

<210> SEQ ID NO 37
<211> LENGTH: 26
<212> TYPE: DNA
<213> ORGANISM: Artificial Sequence
<220> FEATURE:
<223> OTHER INFORMATION: Synthesized

<400> SEQUENCE: 37
actacatgtt ccccacggag gacgag                                           26
```